United States Patent [19]

Nielsen et al.

[11] Patent Number: 5,109,009

[45] Date of Patent: * Apr. 28, 1992

[54] QUINOLINE AND PYRIDINE COMPOUNDS AND INHIBITION OF 5-LIPOXYGENASES THEREWITH

[75] Inventors: Ole Bent T. Nielsen, Vanlose; Ian Ahnfelt-Rønne, Fredensborg, both of Denmark

[73] Assignee: Leo Pharmaceutical Products Ltd., Ballerup, Denmark

[*] Notice: The portion of the term of this patent subsequent to May 2, 2006 has been disclaimed.

[21] Appl. No.: 581,121

[22] Filed: Sep. 10, 1990

Related U.S. Application Data

[63] Continuation of Ser. No. 140,277, Dec. 31, 1987, abandoned, which is a continuation-in-part of Ser. No. 834,542, Feb. 28, 1986.

[30] Foreign Application Priority Data

Mar. 8, 1985 [GB] United Kingdom ............... 8506094
Oct. 11, 1985 [GB] United Kingdom ............... 8525153

[51] Int. Cl.⁵ .............. C07D 215/00; C07D 213/02; A61K 31/47; A61K 31/44
[52] U.S. Cl. .................... 514/311; 514/344; 514/345; 514/351; 546/172; 546/174; 546/177; 546/178; 546/179; 546/180; 546/186; 546/290
[58] Field of Search ............. 514/311, 344, 345, 351; 546/176, 172, 174, 177, 178, 179, 180, 286, 290

[56] References Cited

U.S. PATENT DOCUMENTS 4,661,499 4/1987 Young et al. ............... 546/152

Primary Examiner—David B. Springer
Attorney, Agent, or Firm—Cushman, Darby & Cushman

[57] ABSTRACT

The present invention relates to compounds of formula

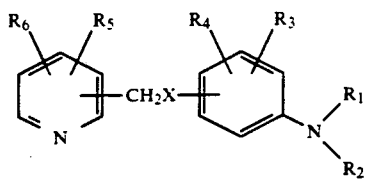

in which formula I X stands for O, S,

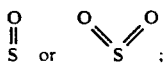

$R_1$ and $R_2$ which can be the same or different stand for hydrogen, straight or branched, saturated or unsaturated, unsubstituted or substituted $C_1$–$C_8$-alkyl, aryl or for ar-$C_1$–$C_4$-alkyl, aryl and ar being unsubstituted or substituted phenyl; $R_3$, $R_4$, $R_5$, and $R_6$ are the same or different and stand for hydrogen, halogen, pseudo halogen, cyano, nitro, amino, carboxy, hydroxy, alkyl, alkoxy; or $R_5$ and $R_6$ form an aromatic ring which is fused to the pyridyl ring, and which aromatic ring may substituted; provided that $R_1$ and $R_2$ cannot be hydrogen at the same time, and provided that when $R_5$ and $R_6$ both are chlorine and $R_1$ is hydrogen, then $R_2$ cannot be n-propyl; and salts and bioreversible derivatives thereof.

The compounds of formula I are useful in the human and veterinary therapy, as they exert specific 5-lipoxygenase inhibition.

13 Claims, No Drawings

QUINOLINE AND PYRIDINE COMPOUNDS AND INHIBITION OF 5-LIPOXYGENASES THEREWITH

This is a continuation of application Ser. No. 07/140,277, filed on Dec. 31, 1987, which was abandoned upon the filing hereof which is a continuation-in-part of Ser. No. 834,542, filed Feb. 28, 1986 now abandoned.

The present invention relates to hitherto unknown compounds useful in the human and veterinary therapy, to pharmaceutically acceptable salts thereof, to bioreversible derivatives thereof, to methods for producing said new compounds, to pharmaceutical compositions containing the new compounds, to dosage units of the compositions, and to methods of treating patients using said compositions and dosage units.

It has recently been discovered that leukotrienes, which are formed via the 5-lipoxygenase pathway of arachidonic acid metabolism, are implicated in a variety of pathophysiologic functions such as bronchoconstriction, plasma exudation, coronary artery spasm, leukocyte chemotaxis and neutrophilic degranulation (for review, see J. L. Marx, Science 215 (1982), 1380–83). It is therefore of considerable interest to develop compounds which inhibit 5-lipoxygenases and thereby the production of leukotrienes. It has surprisingly turned out that the present compounds show a pronounced lipoxygenase inhibitory effect, as discussed below.

The present compounds have the formula I

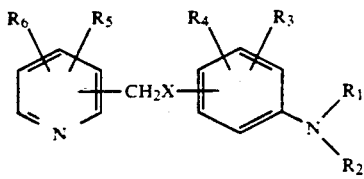

in which formula I X stands for O, S,

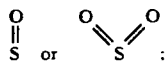

$R_1$ and $R_2$ which can be the same or different stand for hydrogen, straight or branched, saturated or unsaturated, unsubstituted or substituted $C_1$–$C_8$-alkyl, aryl or for ar-$C_1$–$C_4$-alkyl, aryl and ar being unsubstituted or substituted phenyl, the above substitution being with one or more of the following substituents: halogen, pseudo halogen, such as trifluoromethyl, cyano, nitro, amino, carboxy, hydroxy, alkyl, alkoxy; $R_3$, $R_4$, $R_5$, and $R_6$ are the same or different and stand for hydrogen, halogen, pseudo halogen, cyano, nitro, amino, carboxy, hydroxy, alkyl, alkoxy; or $R_5$ and $R_6$ form an aromatic ring which is fused to the pyridyl ring, and which aromatic ring may be substituted with one or more of the following: halogen, pseudo halogen, such as trifluoromethyl, cyano, nitro, amino, carboxy, hydroxy, alkyl, alkoxy; provided that $R_1$ and $R_2$ cannot be hydrogen at the same time, and provided that when $R_5$ and $R_6$ both are chlorine and $R_1$ is hydrogen, then $R_2$ cannot be n-propyl.

Among the preferred compounds of the invention are compounds in which $R_5$ and $R_6$ in formula I form an aromatic ring fused to the pyridine ring, i.e. compounds containing a quinoline ring or an isoquinoline ring, these compounds furthermore being preferred by having the —$NR_1R_2$ and the

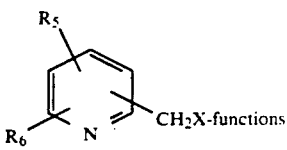

in formula I placed in meta position to each other. Of particular value among compounds having these characteristics are compounds of the invention in which X in formula I is oxygen, in which

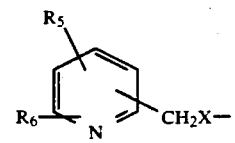

in formula I is a 2-quinolylmethoxy radical, and in which $R_1$ in formula I is hydrogen, these examples, however, not being considered limiting for the invention.

The present salts of the compounds of formula I may be formed with pharmaceutically acceptable inorganic or organic acids, such as hydrochloric, hydrobromic and hydroiodic acid, phosphoric acid, sulphuric acid, nitric acid, p-toluenesulphonic acid, methanesulphonic acid, formic acid, acetic acid, propionic acid, citric acid, tartaric acid, and maleic acid, without these examples being considered limiting for the invention.

In some cases it can be advantageous to prepare suitable bioreversible derivatives of compounds of the invention, i.e. to prepare so-called prodrugs, preferably derivatives, the physicochemical properties of which leads to improved solubility at physiological pH and/or absorption of the compound in question.

Such derivatives are for instance esters of N-hydroxymethyl derivatives of compounds of the invention, such compounds being prepared by reaction of the secondary amine-function of compounds of the invention with formaldehyde (1,2,3,4) followed by reaction with a suitable acidic compound or activated derivatives of such compounds, for instance with bisulfite (5), N,N-dimethylglycine, N,N-diethyl-$\beta$-alanine, or phosphoric acid (6), but other suitable acids which form bioreversible derivatives with desirable physicochemical properties can be used as well.

(1) R. G. Kallen and W. P. Jencks, J. Biol. Chem., 241, 5864, (1966). (2) C. J. Martin and M. A. Marini, J. Biol. Chem., 242, 5736 (1967). (3) M. Levy and D. E. Silberman, J. Biol. Chem., 118, 723 (1937). (4) S. Lewin and D. A. Humphany, J. Chem. Soc. B, 1966, 210. (5) B. C. Jain, B. H. Iyer, and P. C. Guha (Indian Inst. Sci., Bangalore). Science and Culture 11, 568-9 (1946). (6) S. A. Varia, S. Schuller, K. B. Sloan and V. J. Stella, J. Pharm. Sci., 73(8), 1068–1073 (1985) and following papers.

These examples are not to be considered as limiting for the invention, and other suitable methods to improve the physicochemical properties and solubility of the compounds concerned can be used as well.

Metabolites of arachidonic acid include prostaglandins and leukotrienes. Both of these two groups of metabolites are important in the pathophysiology of inflammatory and allergic reactions. Many inhibitors of prostaglandin synthesis are known and are being used as anti-inflammatory agents (7), but relatively few leukotriene synthesis inhibitors are presently known (1), and they are generally not clinically acceptable. The first step in the biochemical synthesis of all leukotrienes is the peroxidation at the 5-carbon atom of arachidonic acid. This reaction is catalyzed by the enzyme 5-lipoxygenase, present mainly in leukocytes. Leukotriene $B_4$ is one of the most potent chemoattractants for polymorphonuclear leukocytes, and at the same time causes aggregation and degranulation of these inflammatory cells. It is thus a potent pro-inflammatory hormone. Leukotriene $C_4$, $D_4$, and $E_4$ together comprise the agent known previously as "slow-reacting substance of anaphylaxis" (SRS-A), which is three orders of magnitude more potent than histamine in causing bronchoconstriction, and also regulates microvascular smooth muscle contractibility and permeability. It is therefore a mediator of asthmatic, allergic and inflammatory reactions.

(7) R. J. Flower, S. Moncada and J. R. Vane. in the Pharmacological Basis of Therapeutics (Ed. A. G. Gilman, L. S. Goodmann and A. Gilman), p. 682–728, Macmillan, New York (1980). (1) M. A. Bray, A. W. Ford-Hutchinson and M. J. H. Smith, in SRS-A and Leukotrienes (Ed. P. J. Piper), p. 253, Wiley, New York (1981).

Inhibition of 5-lipoxygenase thus leads to a decrease in the formation of all of these inflammatory and allergic mediators. This has very important clinical implications, as specific 5-lipoxygenase inhibitors are of potential interest in the therapy of asthma, allergy, rheumatoid arthritis, atherosclerosis, psoriasis and other proliferative skin-disorders, ulcerative colitis and other chronic inflammatory conditions, vasospasm associated with angina pectoris, etc. The identification of specific 5-lipoxygenase inhibitors is thus a novel approach with very wide implications for the treatment of a diversity of clinical disorders.

As stated above, the present compounds have surprisingly been shown to exert such specific 5-lipoxygenase inhibition.

The biological activity of the present compounds was determined both in vitro and in vivo. The following method was used to assay 5-lipoxygenase activity in vitro: Rat peritoneal cells were harvested by i.p. injection of 10 ml Hank's balanced salt solution (GIBCO), cat. No. 4025, U.S.A.) containing 12.5 U/ml sodium heparin (Leo, Denmark) in anaesthesized rats. The resulting cell suspension, which mainly contained macrophages, was transferred to a test tube and washed twice by centrifugation (200 g, 10 min.) and resuspended in Hank's balanced salt solution containing 0.5% bovine serum albumin (Sigma Chem. Co., U.S.A.). The cells from 6 rats were finally resuspended in Hank's balanced salt solution containing 5 $\mu$Ci (1-$^{14}$C) arachidonic acid (The Radiochemical Centre, Amersham, U.K.) and incubated for 90 minutes at 30° C. This caused labelling of cell membrane phospholipids as radioactive arachidonic acid was incorporated in the 2-position of the glycerol moiety. Excess arachidonic acid was then removed by washing the cells twice as described above. The cells were finally resuspended in the same solution at $10^7$ cells/ml. 475 $\mu$l of the cell suspension was preincubated at 37° C. for 5 minutes with either 5 $\mu$l DMSO (control tube), or 5 $\mu$l of a drug solution in DMSO. Then 20 $\mu$l of a mixture of equal volumes of the calcium ionophore A 23187, $10^{-4}$M in ethanol (Calbiochem, U.S.A.), and 0.5M $CaCl_2$ in water was added. The final concentration of A 23187 was thus $2 \times 10^{-6}$M, and of $Ca^{++}$ 8 mM. After minutes of incubation the tubes were transferred to an ice-bath and centrifugated for 10 minutes at 3,000 g (4° C.). An aliquot of the supernatant was counted by liquid scintillation spectrometry in order to calculate the total radioactive release induced by A 23187 in presence of drugs. A decrease in radioactive release was taken as indication of phospholipase $A_2$-inhibition. The supernatant was then extracted twice with ethyl acetate (2 ml), adjusted to pH 3 with 1N HCl and further extracted with $2 \times 2$ ml ethyl acetate. The combined extracts were evaporated to dryness in vacuo, the residue was redissolved in a small volume of methanol and applied by means of a Desage Autospotter TM to a silica-gel coated thin-layer plate fitted with a polar concentrating zone (Merck Art. 11798, Darmstadt, FRG). The plates were developed in the organic layer of the solvent mixture ethyl acetate/acetic acid/iso-octane/water (55:10:25:50). Radioactive spots were detected by autoradiography (AGFA-GEVAERT, Osray-RPI X-ray film, Belgium), and changes induced by drugs in the metabolic pattern of arachidonic acid were quantified by a laser densitometer. (LKB, Ultroscan TM 2202, Bromma, Sweden) in combination with an integrating computer (SP 4100, Spectra-Physics, San José, Calif., U.S.A.).

These cells produced measurable amounts of radioactive 6-keto-prostaglandin $F_{1\alpha}$, thromboxane $B_2$, prostaglandin $D_2$, hydroxyheptadecatrienoic acid (HHT) (all cyclooxygenase products), 5-hydroxyeicosatetraenoic acid (5-HETE) and leukotriene $B_4$ (both 5-lipoxygenase products).

When OT 3447 (Example 2C) at final concentrations from $10^{-6}$M and above was added to the reaction mixture described above, a significant and specific decrease in the production of leukotriene $B_4$ and 5-HETE occurred. At the same time, the synthesis of the cyclooxygenase products HHT, prostaglandin $D_2$ and thromboxane $B_2$ and 6-keto-prostaglandin $F_{1\alpha}$ was not affected, and the synthesis of 6-keto-prostaglandin $F_{1\alpha}$, the stable metabolite of prostacyclin, was accelerated. This pattern of drug activity is indicative of truly specific 5-lipoxygenase inhibition.

Two in vivo methods were used to assess the effect of either oral or parenteral administration of the compounds to experimental animals on the release of leukotrienes. In the first method, calcium ionophore A 23187 was injected into the peritoneal cavity of adrenalectomized and anaestesized rats. 5 minutes later the cavity was washed, and the leukotrienes were extracted with ethanol and redissolved in water or buffer. The amount of leukotriene $D_4$ released in response to A 23187 was determined by bioassay, using the contraction of an isolated guinea-pig ileum-strip as indicator. Leukotriene $C_4$ and $B_4$ were measured by commercially available radioimmunoassays (New England Nuclear, Dreieich, West Germany, and The Radiochemical Centre, Amersham, U.K., respectively). By all 3 assays a substantial inhibition of leukotriene formation was observed following administration of OT 3447 (Example 2C) prior to intraperitoneal injection of A 23187.

The other method was used to measure a physiological consequence of leukotriene release in the lungs, an asthmatic attack. Guinea-pigs hypersensitive to ovalbumin were anaestesized and mechanically ventilated with a constant airvolumen ad modum Konzett-Rössler. The animals were pretreated with mepyramine, indomethacin and propranolol to avoid interference with endogenous production of histamine, prostaglandins and $\beta$-adrenergic mechanisms, respectively. They were then challenged with an intravenous injection of ovalbumin, and the increase in airway resistance was measured by the respiratory overflow. Pretreatment of the animals with OT 3447 (Example 2C) significantly reduced the asthmatic reaction, indicating a clinically beneficial effect of inhibiting endogenous leukotriene release by the administration of these compounds.

Antagonism of leukotriene mediated effects at the receptor level, in addition to inhibition of leukotriene synthesis, is an additional mode of action of some of the present compounds. Obviously, this dual mechanism is of potentially great interest in preventing leukotriene mediated reactions.

Leukotriene antagonists may be identified by observing the contractions elicited in preparations of guinea-pig ileum strips suspended in physiological buffers by addition of pure leukotriene $D_4$. The ileum strips are connected to an isotonic transducer, and the contractions are continuously recorded on a multichannel recorder.

Before addition of leukotriene $D_4$, atropine and indomethacin are added to the buffer in order to block any cholinergic or prostaglandin-mediated contractile effects. Test compounds to be studied with respect to leukotriene antagonism are dissolved in dimethylsulphoxide (DMSO) and added to the organ bath 2 minutes prior to addition of leukotriene $D_4$ at $10^{-9}M$ (final concentration), the final concentration of DMSO being 0.1%, a concentration which can be shown not to affect the ileum response to leukotriene $D_4$. The test compounds may be added at various concentrations, often beginning at $10^{-6}M$ and then decreasing the concentration in case of antagonism.

When the compounds of the present invention were added to the ileum preparation before addition of leukotriene $D_4$ a significant inhibition occurred of the specific leukotriene $D_4$-induced contraction. In several cases this inhibition occurred at concentrations in the submicromolar range, e.g. Examples 39, 11 (part A), 11 (part C), 18, 23, 22, and 78 (part C).

On the other hand, contractions induced with histamine at $10^{-6}M$ were not inhibited by these compounds even at micromolar concentrations.

Products formed by the enzyme responsible for the first step in leukotriene synthesis, 5-lipoxygenase, which is probably the target enzyme of compounds of the present invention, play a role as mediators of mast cell degranulation. One of the effects of mast cell degranulation is the release of histamine. Thus, 5-lipoxygenase inhibitors may suppress histamine release from mast cells.

In order to investigate this possibility, cells obtained from washings of the peritoneal cavity of rats, were studied. These peritoneal washings contain mainly macrophages and mast cells. The mast cells were passively sensitized with IgE-antibodies to ovalbumin, and then challenged with the antigen, ovalbumin, to induce histamine release. Alternatively, the unsensitized mast cells were exposed to an ionophore, compound 48/80*, which induces histamine release independently of immunologic mechanisms. Histamine released to the medium after degranulation of the peritoneal mast cells was measured by a fluorometric method.
*(the condenstion product of N-methyl-p-methoxyphenethylamine with formaldhyde)

Several of the compounds of the present invention inhibited histamine release from mast cells (see Table I below).

TABLE I

Effect of compounds of the invention on rat peritoneal mast cell histamine release

| Compound[a] according to | Inhibition (%) of histamine release induced by | |
|---|---|---|
| | Antigen | Cp. 48/80 |
| Ex. 10, part C | 51 | 19 |
| Ex. 39 | 100 | 95 |
| Ex. 38 | 91 | 85 |
| Ex. 22 | 100 | 75 |
| Ex. 68 | 45 | 17 |
| Ex. 78, part C | 96 | 95 |
| Ex. 79, part C | 100 | 95 |
| Ex. 70 | 100 | 45 |
| Ex. 77 | 100 | 92 |
| Ex. 66 | 100 | 65 |

[a]The compounds were studied at 10 μM concentrations

There was a tendency for stronger inhibition of antigen than cp. 48/80-induced histamine release, in agreement with the postulated role for 5-lipoxygenase products in immunologically mediated mast cell degranulation. The present observation further demonstrates the efficacy of the compounds of the invention in suppressing anaphylactic reactions.

The present invention also relates to a method for producing the present compounds.

In one embodiment, an amine of the formula II

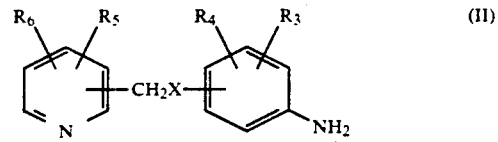

in which $R_3$, $R_4$, $R_5$, $R_6$ and X have the above meanings, is reacted with a compound of the formula III

$$R_2Y \qquad (III)$$

in which $R_2$ has the above meanings except hydrogen and Y is capable of forming a "good leaving group", Y thus standing for e.g. a halogen atom, such as chlorine, bromine or iodine, or an alkyl- or arylsulphonyloxy group, but other leaving groups can be used as well, such as an alkylsulphate group, a chlorosulphonyloxy group, an alkylsulphite group, a mono- or dialkylphosphate group or a nitrate group, to form a compound of the formula I in which $R_1$ stands for hydrogen.

The reaction is performed in a suitable inert organic solvent, such as methanol, ethanol, dimethylformide or hexamethyl phosphoric triamide, but other solvents can be used as well; the reaction is performed at a temperature about or above room temperature, up to the boiling point of the solvent used. In some cases it can, however, be convenient to cool the reaction mixture below room temperature, depending on the nature of the compound of the formula III used. The reaction is also conveniently performed in the presence of an organic base, such as pyridine, triethylamine, sodium methanolate or sodium ethanolate or in the presence of a suitable inorganic base, such as an alkalimetal hydroxide, an alkalimetal carbonate or an alkalimetal hydrogen carbonate, but other bases can be used as well. The crude reaction products of the formula I are collected by filtration, if convenient after dilution with e.g. water, or are extracted from the reaction mixture with a suitable solvent, such as diethyl ether, ethyl acetate, dichloromethane or chloroform. The products are purified e.g. by recrystallization or by chromatography, if convenient after conversion to salts with suitable in-organic or organic acids as defined above.

In another embodiment, an amine of the formula II is converted to a compound of the formula I, in which $R_1$ stands for hydrogen by reductive alkylation, e.g. by reaction with a carbonyl compound of the formula IV

(IV)

in which $R_7$, $R_8$, and the carbonyl function together are capable of forming a substituent $R_2$ with the above meanings, followed by hydrogenation in the presence of a suitable catalyst or by reduction e.g. with an alkali-metal borohydride. The hydrogenation or reduction can, if convenient, be performed simultaneously with the reaction with the carbonyl compound, that is, without isolation of the intermediary, so called Schiff-base.

The reaction is performed in a suitable inert organic solvent, such as methanol or ethanol, but other solvents can be used as well. The reaction is preferably performed at ambient temperature, but in some cases it is convenient to cool the reaction mixture below room temperature, or to heat the reaction mixture above room temperature, up to the boiling point of the solvent used, depending on the nature of the reactants of the formulae II and IV used. The isolation and purification of the products can be performed as described above.

If a compound of the formuls I, in which $R_1$ is different from hydrogen, is desired, the above compounds of formula I in which $R_1$ stands for hydrogen can be further alkylated by reaction with a compound of the formula V $R_1Y$ (V)

in which $R_1$ and Y have the above meanings, except that $R_1$ cannot be hydrogen. The solvents and reaction conditions used are preferably as described above.

The introduction of the substituents $R_1$ and $R_2$ can be performed simultaneously, e.g. when $R_1 = R_2$, but also when $R_1$ and $R_2$ are different, the reaction can be performed without isolation of the monoalkylated intermediate.

In still another embodiment a compound of the formula VII

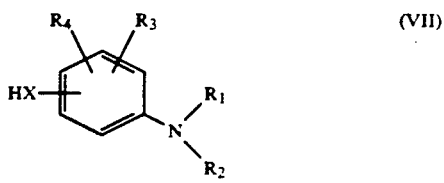
(VII)

in which $R_1$, $R_2$, $R_3$, and $R_4$ have the above meanings, and X stands for oxygen or sulfur, is reacted with a compound of the formula VIII

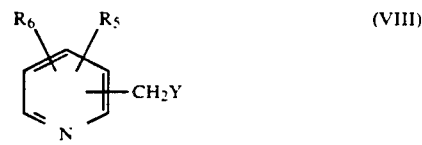
(VIII)

in which $R_5$, $R_6$ and Y have the above meanings, to form the desired compound of formula I.

The solvent and reaction conditions used are conveniently as described above for the alkylation of amines of the formula II, but other solvent and/or reaction conditions can be used as well, depending on the nature of the compounds of the formulae VII and VIII which are reacted.

Another embodiment is described in the following reaction scheme:

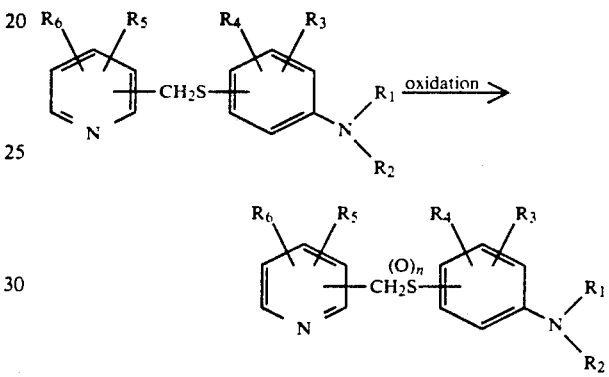

in which n stands for 1 or 2, $R_1$, $R_2$, $R_3$, $R_4$, $R_5$, and $R_6$ have the above meanings.

If $R_1$, $R_2$, $R_3$, $R_4$, $R_5$, or $R_6$ are or contain substituents, which can react under the above mentioned conditions, such $R_1$, $R_2$, $R_3$, $R_4$, $R_5$, or $R_6$ are protected in usual manner before the reaction, and deprotected afterwards.

The present compounds are intended for use in pharmaceutical compositions which are useful in the treatment of asthma, allergy, rheumatoid arthritis, atherosclerosis, psoriasis and other proliferative skin-disorders, ulcerative colitis and other inflammatory conditions, vasospasms, etc.

The amount required of a compound of formula (I) (hereinafter referred to as the active ingredient) for therapeutic effect will, of course, vary both with the particular compound, the route of administration and the mammal under treatment. A suitable dose of a compound of formula (I) for a mammal suffering from e.g. an inflammatory condition as defined hereinbefore is 0.5 to 100 mg per kilogram bodyweight, the most preferred dosage being 0.5 to 50 mg/kg of mammal bodyweight, for example 5 to 25 mg/kg; administered once or more times daily.

In the case of the treatment or prophylaxis of inflammatory airway conditions, a suitable anti-asthmatic dose of a compound of formula (I) is 1 μg to 50 mg of compounds per kilogram bodyweight, the most preferred dosage being 1 μg to 10 mg/kg of mammal bodyweight, for example from 1 μg to 5 mg/kg.

While it is possible for an active ingredient to be administered alone as the raw chemical, it is preferable to present it as a pharmaceutical formulation. Conveniently, the active ingredient comprises form 0.1% to 100% by weight of the formulation. Conveniently, dosage units of a formulation contain between 0.1 mg and 1 g of the active ingredient. For topical administration, the active ingredient preferably comprises from 1% to 2% by weight of the formulation but the active ingredient may comprise as much as 10% w/w. Formulations suitable for nasal or buccal administration, (such self-propelling powder-dispensing formulations described hereinafter), may comprise 0.1 to 20% w/w, for example about 2% w/w of active ingredient.

By the term "dosage unit" is meant a unitary, i.e. a single dose which is capable of being administered to a patient, and which may be readily handled and packed, remaining as a physically and chemically stable unit dose comprising either the active material as such or a mixture of it with solid or liquid pharmaceutical diluents or carriers.

The formulations, both for veterinary and for human medical use, of the present invention comprise an active ingredient in association with a pharmaceutically acceptable carrier therefor and optionally other therapeutic ingredient(s). The carrier(s) must be "acceptable" in the sense of being compatible with the other ingredients of the formulations and not deleterious to the recipient thereof.

The formulations include those in a form suitable for oral, ophthalmic, rectal, parenteral (including subcutaneous, intramuscular and intravenous), intra-articular, topical, nasal or buccal administration.

The formulations may conveniently be presented in dosage unit form and may be prepared by any of the methods well known in the art of pharmacy. All methods include the step of bringing the active ingredient into association with the carrier which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion. The active ingredient may also be administered in the form of a bolus, electuary or paste.

A tablet may be made by compressing or moulding the active ingredient optionally with one or more accessory ingredient. Compressed tablets may be prepared by compressing, in a suitable machine, the active ingredient in a free-flowing form such as a powder or granules, optionally mixed with a binder, lubricant, inert diluent, surface active or dispersing agent. Moulded tablets may be made by moulding, in a suitable machine, a mixture of the powdered active ingredient and a suitable carrier moistened with an inert liquid diluent.

Formulations for rectal administration may be in the form of a suppository incorporating the active ingredient and a carrier such as cocoa butter, or in the form of an enema.

Formulations suitable for parenteral administration conveniently comprise a sterile oily or aqueous preparation of the active ingredient which is preferably isotonic with the blood of the recipient.

Formulations suitable for intra-articular administration may be in the form of a sterile aqueous preparation of the active ingredient which may be in microcrystalline form, for example, in the form of an aqueous microcrystalline suspension. Liposomal formulations or biodegradable polymer systems may also be used to present the active ingredient for both intra-articular and ophthalmic administration.

Formulations suitable for topical administration include liquid or semi-liquid preparations such as liniments, lotions, applications; oil-in-water or water-in-oil emulsions such as creams, ointments or pastes; or solutions or suspensions such as drops. For example, for ophthalmic administration, the active ingredient may be presented in the form of aqueous eye drops as, for example, a 0.1–1.0% solution.

Formulations suitable for administration to the nose or buccal cavity include powder, self-propelling and spray formulations such as aerosols and atomizers. The formulations, when dispersed, preferably have a particle size in the range of 10 to 100$\mu$.

Such formulations are most preferably in the form of a finely comminuted powder for pulmonary administration from a powder inhalation device or self-propelling powder-dispensing formulations, where the active ingredient, as a finely comminuted powder, may comprise up to 99.9% w/w of the formulation. In the case of self-propelling solution and spray formulations, the effect may be achieved either by choice of a valve having the desired spray characteristics (i.e. being capable of producing a spray having the desired particle size) or by incorporating the active ingredient as a suspended powder in controlled particle size. These self-propelling formulations may be either powder-dispensing formulations or formulations dispensing the active ingredient as droplets of a solution or suspension.

Self-propelling powder-dispensing formulations preferably comprise dispersed particles of solid active ingredients, and a liquid propellant having a boiling point below 18° C. at atmospheric pressure. The liquid propellant may be any propellant known to be suitable for medicinal administration and may comprise one or more lower alkyl hydrocarbons or halogenated lower alkyl hydrocarbons or mixtures thereof; chlorinated and fluorinated lower alkyl hydrocarbons are especially preferred. Generally, the propellant constitutes 50 to 99.9% w/w of the formulation whilst the active ingredient constitutes 0.1 to 20% w/w, for example about 2% w/w, of the formulation.

The pharmaceutically acceptable carrier in such self-propelling formulations may include other constituents in addition to the propellant, in particular a surfactant or a solid diluent or both. Surfactants are desirable since they prevent agglomeration of the particles of active ingredient and maintain the active ingredient in suspension. Especially valuable are liquid non-ionic surfactants and solid anionic surfactants or mixtures thereof. Suitable liquid non-ionic surfactants are esters and partial esters of fatty acids with aliphatic polyhydric alcohols, for instance, sorbitan monooleate and sorbitan trioleate, known commercially as "Span 80" (Trade Name) and "Span 85" (Trade Name), respectively. The liquid non-ionic surfactant may constitute from 0.01 up to 20% w/w of the formulation, though preferably it constitutes below 1% w/w of the formulation. Suitable solid anionic surfactants include alkali metal, ammonium and amine salts of dialkyl sulphosuccinate (where the alkyl groups have 4 to 12 carbon atoms). The solid anionic surfactants may constitute from 0.01 up to 20% w/w of the formulation, though preferably below 1% w/w of the composition solid diluents may be advantageously incorporated in such self-propelling formulation where the density of the active ingredient differs substantially from the density of the propellant; also, they help to maintain the active ingredient in suspension. The solid diluent is in the form of a fine powder, preferably having a particle size of the same order as that of the particles of the active ingredient. Suitable solid diluents include sodium chloride, sodium sulphate and sugars.

Formulations of the present invention may also be in the form of a self-propelling formulation wherein the active ingredient is present in solution. Such self-propelling formulations may comprise the active ingredient, propellant and co-solvent, and advantageously an antioxidant stabiliser. The propellant is one or more of these already cited above. Co-solvents are chosen for their solubility in propellant, their ability to dissolve the active ingredient, and for their having the lowest boiling point consistent with these above-mentioned properties. Suitable co-solvents are lower alkyl alcohols and ethers and mixtures thereof. The co-solvent may constitute 5 to 40% w/w of the formulation, though preferably less than 20% w/w of the formulation. Antioxidant stabilisers may be incorporated in such solutions-formulations to inhibit deterioration of the active ingredient and are conveniently alkali metal ascorbates or bisulphites. They are preferably present in an amount of up to 0.25% w/w of the formulation.

Such self-propelling formulations may be prepared by any method known in the art. For example, the active ingredient (either as particles as defined hereinbefore in suspension in a suitable liquid or in up to 20% w/v solution in an acceptable co-solvent, as appropriate) is mixed with any other constituents of a pharmaceutically acceptable carrier. The resulting mixture is cooled, introduced in a suitable cooled container and propellant is added thereto in liquid form; and the container is sealed. Alternatively, such self-propelling formulations may be prepared by mixing the active ingredient either in particles as hereinbefore defined or in 2 to 20% w/v alcohol or aqueous solution as appropriate, together with the remaining constituents of the pharmaceutically acceptable carrier other than the propellant; introducing the resulting mixture, optionally with some propellant, into a suitable container; and injecting the propellant, under pressure, into the container at ambient temperature through a valve which comprises a part of the container and is used to control release of the formulation from it. Desirably, the container is purged by removing air from it at a convenient stage in the preparation of the self-propelling formulation.

A suitable container for a self-propelling formulation is one provided with a manually-operable valve and constructed of aluminium, stainless steel or reiforced glass. The valve should, of course, be one having the desired spray characteristics of particle size as hereinbefore defined. Advantageously, the valve is of the type which delivers a fixed amount of the formulation on the occasion of each operation of the valve, for example, about 50 to 100 microliters of formulation in each delivery.

Formulations of the present invention may also be in the form of an aqueous or dilute alcoholic solution, optionally a sterile solution, of the active ingredient for use in a nebuliser or atomizer, wherein an accelerated air stream is used to produce a fine mist consisting of small droplets of the solution. A buffering agent and a surface active agent may also be included in such a formulation which should also contain a preservative such as methylhydroxybenzoate.

Other formulations suitable for nasal administration include a fine powder having a particle size of 10 to 100 microns which is administered in the manner in which snuff is taken, i.e. by rapid inhalation through the nasal passage from a container of the powder held close up to the nose.

In addition to the aforementioned ingredients, the formulations of this invention may include one or more additional ingredients such as diluents, buffers, flavouring agents, binders, surface active agents, thickeners, lubricants, preservatives, e.g. methylhydroxybenzoate (including anti-oxidants), emulsifying agents and the like.

The compositions may further contain other therapeutically active compounds usually applied in the treatment of the above mentioned pathological conditions, for instance glucocorticoids, anti-histamines, anticholinergic agents, methyl xanthines. $\beta$-adrenergic agents, salicylates, indomethacin, flufenamate, naproxen, timegadine, gold salts, penicillamine, serum cholesterol-reducing agents, retinoids, zinc salts, and salicylazosulfapyridin (Salazopyrin).

According to the invention, the present compounds are administered to a patient suffering from one of the above mentioned pathological conditions in a daily dose (for adults) from 0.1 mg to 7000 mg, preferably from 35-3500 mg, and in the veterinary practice correspondingly in daily doses from 0.5 to 100 mg/kg bodyweight.

The invention will now be further described in the following non-limiting Examples:

EXAMPLE 1

4-(4'-Pyridylmethoxy)-N-methylaniline

A. 4-(4'-Pyridylmethoxy)acetanilide

A mixture of 4-acetaminophenol (30.5 g), 4-chloromethylpyridine hydrochloride (40 g), potassium carbonate (85 g) and dimethylformamide (400 ml) is stirred at ambient temperature for about 20 hours and is finally stirred at 60°-80° C. for a further 3-4 hours. The resulting mixture is diluted with water to precipitate the product, which is filtered off, washed with water and dried in air. An analytically pure sample has a melting point of 165°-67° C.

B. 4-(4'-Pyridylmethoxy)aniline

A mixture of 4-(4'-pyridylmethoxy)acetanilide (40 g), 4N hydrochloric acid (400 ml) and ethanol (100 ml) is refluxed for 3 hours. After cooling, the resulting solution is neutralized to pH 8 with a solution of sodium hydroxide to precipitate the product, which is filtered off, washed with water and dried in air. It is obtained as a hydrate with a melting point of 130°-131° C.

C. 4-(4'-Pyridylmethoxy)-N-methylaniline

To a solution of sodium methoxide (prepared from 2.3 g of sodium) in methanol (30 ml) is added 4-(4'-pyridylmethoxy)aniline (4.0 g) followed by paraformaldehyde (0.85 g), and the mixture is stirred at ambient temperature for 5 hours. Sodium borohydride (0.7 g) is then added, and the mixture is stirred at ambient temperature for a further 12 hours and is finally refluxed for 1 hour. 2N Sodium hydroxide (30 ml) is added, and the mixture is refluxed for 2 hours, and is then cooled and extracted twice with ethylacetate. The extract is evaporated and the resulting product recrystallized from acetone/water to give the title compound with a melting point of 129°–131° C.

EXAMPLE 2

4-(3'-Pyridylmethoxy)-N-methylaniline

A. 4-(3'-Pyridylmethoxy)acetanilide

By following the procedure of Example 1, part A, but replacing 4-chloromethylpyridine hydrochloride with 3-chloromethylpyridine hydrochloride, the title compound is obtained.

B. 4-(3'-Pyridylmethoxy)aniline

By following the procedures of Example 1, part B, but replacing 4-(4'-pyridylmethoxy)acetanilide with 4-(3'-pyridylmethoxy)acetanilide, the title compound is obtained as a hydrate with a melting point of 72°–75° C.

C. 4-(3'-Pyridylmethoxy)-N-methylaniline

By following the procedure of Example 1, part C, but replacing 4-(4'-pyridylmethoxy)aniline with 4-(3'-pyridylmethoxy)aniline, the title compound is obtained. It is conveniently isolated as the dihydrochloride, having a melting point of 212° C.

EXAMPLE 3

4-(2'-Pyridylmethoxy)-N-methylaniline

A. 4-(2'-Pyridylmethoxy)acetanilide

By following the procedure of Example 1, part A, but replacing 4-chloromethylpyridine hydrochloride with 2-chloromethylpyridine hydrochloride, the title compound is obtained.

B. 4-(2'-Pyridylmethoxy)aniline

By following the procedure of Example 1, part B, but replacing 4-(4'-pyridylmethoxy)acetanilide with 4-(2'-pyridylmethoxy)acetanilide, the title compound is obtained as an oil.

C. 4-(2'-Pyridylmethoxy)-N-methylaniline

By following the procedure of Example 1, part C, but replacing 4-(4'-pyridylmethoxy)aniline with 4-(2'-pyridylmethoxy)aniline, the title compound is obtained with a melting point of 135°–137° C. It can further be isolated as the dihydrochloride having a melting point of 187°–189° C.

EXAMPLE 4

3-(4'-Pyridylmethoxy)-N-methylaniline

A. 3(4'-Pyridylmethoxy)acetanilide

By following the procedure of Example 1, part A, but replacing 4-acetaminophenol with 3-acetaminophenol, the title compound is obtained.

B. 3-(4'-Pyridylmethoxy)aniline

By following the procedure of Example 1, part B, but replacing 4-(4'-pyridylmethoxy)acetanilide with 3-(4'-pyridylmethoxy)acetanilide, the title compound is obtained with a melting point of 114°–116° C.

C. 3-(4'-Pyridylmethoxy)-N-methylaniline

By following the procedure of Example 1, part C, but replacing 4-(4'-pyridylmethoxy)aniline with 3-(4'-pyridylmethoxy)aniline, the title compound is obtained.

It is isolated as a hemihydrate of the dihydrochloride having a melting point of 211°–214° C.

EXAMPLE 5

3-(3'-Pyridylmethoxy)-N-methylaniline

A. 3-(3'-Pyridylmethoxy)acetanilide

By following the procedure of Example 1, part A, but replacing 4-acetaminophenol with 3-acetaminophenol, and 4-chloromethylpyridine hydrochloride with 3-chloromethylpyridine hydrochloride, the title compound is obtained.

B. 3-(3'-Pyridylmethoxy)aniline

By following the procedure of Example 1, part B, but replacing 4-(4'-pyridylmethoxy)acetanilide with 3-(3'-pyridylmethoxy)acetanilide, the title compound is obtained with a melting point of 99°–100° C.

C. 3-(3'-Pyridylmethoxy)-N-methylaniline

By following the procedure of Example 1, part C, but replacing 4-(4'-pyridylmethoxy)aniline with 3-(3'-pyridylmethoxy)analine, the title compound is obtained. It is isolated as the dihydrochloride with a melting point of 179°–182° C.

EXAMPLE 6

3-(2'-Pyridylmethoxy)-N-methylaniline

A. 3-(2'-Pyridylmethoxy)acetanilide

By following the procedure of Example 1, part A, but replacing 4-acetaminophenol with 3-acetaminophenol, and 4-chloromethylpyridine hydrochloride with 2-chloromethylpyridine hydrochloride, the title compound is obtained with a melting point of 160°–163° C.

B. 3-(2'-Pyridylmethoxy)aniline

By following the precedure of Example 1, part B, but replacing 4-(4'-pyridylmethoxy)acetanilide with 3-(2'-pyridylmethoxy)acetanilide, the title compound is obtained as a dihydrate with a melting point of 96° C.

C. 3-(2'-Pyridylmethoxy)-N-methylaniline

By following the procedure of Example 1, part C, but replacing 4-(4'-pyridylmethoxy)aniline with 3-(2'-pyridylmethoxy)aniline, the title compound is obtained. It is isolated as the dihydrochloride with a melting point of 195°–198° C.

EXAMPLE 7

2-(4'-Pyridylmethoxy)-N-methylaniline

A. 2-(4'-Pyridylmethoxy)acetanilide

By following the procedure of Example 1, part A, but replacing 4-acetaminophenol with 2-acetaminophenol, the title compound is obtained.

B. 2-(4'-Pyridylmethoxy)aniline

By following the procedure of Example 1, part B, but replacing 4-(4'-pyridylmethoxy)acetanilide with 2-(4'-pyridylmethoxy)acetanilide, the title compound is obtained.

C. 2-(4'-Pyridylmethoxy)-N-methylaniline

By following the procedure of Example 1, part C, but replacing 4-(4'-pyridylmethoxy)aniline with 2-(4'-pyridylmethoxy)aniline, the title compound is obtained.

EXAMPLE 8

2-(3'-Pyridylmethoxy)-N-methylaniline

A. 2-(3'-Pyridylmethoxy)acetanilide

By following the procedure of Example 1, part A, but replacing 4-acetaminophenol with 2-acetaminophenol, and 4-chloromethylpyridine hydrochloride with 3-chloromethylpyridine hydrochloride, the title compound is obtained.

B. 2-(3'-Pyridylmethoxy)aniline

By following the procedure of Example 1, part B, but replacing 4-(4'-pyridylmethoxy)acetanilide with 2-(3'-pyridylmethoxy)acetanilide, the title compound is obtained.

C. 2-(3'-Pyridylmethoxy)-N-methylaniline

By following the procedure of Example 1, part C, but replacing 4-(4'-pyridylmethoxy)aniline with 2-(3'-pryridylmethoxy)aniline, the title compound is obtained.

EXAMPLE 9

2-(2'-Pyridylmethoxy)-N-methylaniline

A. 2-(2'-Pyridylmethoxy)acetanilide

By following the procedure of Example 1, part A, but replacing 4-acetaminophenol with 2-acetaminophenol, and 4-chloromethylpyridine hydrocholoride, with 2-chloromethylpyridine hydrochloride, the title compound is obtained.

B. 2-(2'-Pyridylmethoxy)aniline

By following the procedure of Example 1, part B, but replacing 4-(4'-pyridylmethoxy)acetanilide with 2-(2'-pyridylmethoxy)acetanilide, the title compound is obtained.

C. 2-(2'-Pyridylmethoxy)-N-methylaniline

By following the procedure of Example 1, part C, but replacing 4-(4'-pyridylmethoxy)aniline with 2-(2'-pyridylmethoxy)aniline, the title compound is obtained.

EXAMPLE 10

4-(2'-Quinolylmethoxy)-N-methylaniline

A. 4-(2'-Quinolylmethoxy)acetanilide

By following the procedure of Example 1, part A, but replacing 4-chloromethylpyridine hydrochloride with 2-chloromethylquinoline hydrochloride, the title compound is obtained with a melting point of 178°–180° C.

B. 4-(2'-Quinolylmethoxy)aniline

By following the procedure of Example 1, part B, but replacing 4-(4'-pyridylmethoxy)acetanilide with 4-(2'-quinolylmethoxy)acetanilide, the title compound is obtained with a melting point of 132°–133° C.

C. 4-(2'-Quinolylmethoxy)-N-methylaniline

By following the procedure of Example 1, part C, but replacing 4-(4'-pyridylmethoxy)aniline with 4-(2'-quinolylmethoxy)aniline, the title compound is obtained. It is isolated as a hemihydrate of the dihydrochloride having a kmelting point of 225° C.

EXAMPLE 11

3-(2'-Quinolylmethoxy)-N-methylaniline

A. 3-(2'-Quinolylmethoxy)acetanilide

By following the procedure of Example 1, part A, but replacing 4-acetaminophenol with 3-acetaminophenol, and 4-chloromethylpyridine hydrochloride with 2-chloromethylquinoline hydrochloride, the title compound is obtained a trihydrate with a melting point of 160°–162° C.

B. 3-(2'-Quinolylmethoxy)aniline

By following the procedure of Example 1, part B, but replacing 4-(4'-pyridylmethoxy)acetanilide with 3-(2'-quinolylmethoxy)acetanilide the title compound is obtained as a dihydrate with a melting point of 98° C.

C. 3-(2'-Quinolylmethoxy)-N-methylaniline

By following the procedure of Example 1, part C, but replacing 4-(4'-pyridylmethoxy)aniline with 3-(2'-quinolylmethoxy)aniline, the title compound is obtained. It is isolated as a hemihydrate of the dihydrochloride with a melting point of 227° C.

EXAMPLE 12

2-Chloro-4-(4'-pyridylmethoxy)-N-methylaniline

A. 2-Chloro-4-(4'-pyridylmethoxy)acetanilide

By following the procedure of Example 1, part A, but replacing 4-acetaminphenol with 3-chloro-4-acetaminophenol, the title compound is obtained as a hydrate with a melting point of 126°–128° C.

B. 2-Chloro-4-(4'-pyridylmethoxy)aniline

By following the procedure of Example 1, part B, but replacing 4-(4'-pyridylmethoxy)acetanilide with 2-chloro-4-(4'-pyridylmethoxy)acetanilide, the title compound is obtained with a melting point of 120°–° C.

C. 2-Chloro-4-(4'-pridylmethoxy)-N-methylaniline

By following the procedure of Example 1, part C, but replacing 4-(4'-pyridylmethoxy)aniline with 2-chloro-4-(4'-pyridylmethoxy)aniline, the title compound is obtained.

EXAMPLE 13

3-Chloro-4-(4'-pyridylmethoxy)acetaniline

A. 3-Chloro-4-(4'-pyridylmethoxy)aniline

By following the procedure of Example 1, part A, but replacing 4-acetaminophenol with 2-chloro-4-acetaminophenol, the title compound is obtained.

B. 3-Chloro-4-(4'-pyridylmethoxy)aniline

By following the procedure of Example 1, part A, but replacing 4-(4'-pyridylmethoxy)acetanilide with 3-chloro-4-(4'-pyridylmethoxy)acetanilide, the title compound is obtained as a dihydrate with a melting point of 94°–96° C.

C. 3-Chloro-4-(4'-pyridylmethoxy)-N-methylaniline

By following the procedure of Example 1, part C, but replacing 4-(4'-pyridylmethoxy)aniline with 3-chloro-4-(4'-pyridylmethoxy)aniline, the title compound is obtained.

EXAMPLE 14

2,3-Dichloro-4-(4'-pyridylmethoxy)-N-methylaniline

A. 2,3-Dichloro-4-(4'-pyridylmethoxy)acetanilide

By following the procedure of Example 1, part A, but replacing 4-acetaminophenol with 2,3-dichloro-4-acetaminophenol, the title compound is obtained as a hydrate with a melting point of 159°-161° C.

B. 2,3-Dichloro-4-(4'-pyridylmethoxy)aniline

By following the procedure of Example 1, part B, but replacing 4-(4'-pyridylmethoxy)acetanilide with 2,3-dichloro-4-(4'-pyridylmethoxy)acetanilide, the title compound is obtained with a melting point of 123°-124° C.

C. 2,3-Dichloro-4-(4'-pyridylmethoxy)-N-methylaniline

By following the procedure of Example 1, part C, but replacing 4-(4'-pyridylmethoxy)aniline with 2,3-dichloro-4-(4'-pyridylmethoxy)aniline, the title compound is obtained with a melting point of 160°-162° C.

EXAMPLE 15

4-(4-Pyridylmethoxy)-N,N-dimethylaniline

To a solution of 4-(4'-pyridylmethoxy)aniline (10.0 g; prepared as described in Example 1, part B) in hexamethyl phosphoric triamide (50 ml) is added sodium hydrogen carbonate (12.5 g) followed by methyl iodide (14.2 g), and the mixture is stirred at ambient temperature for 12 hours. The product is precipitated by dilution with water (about 500 ml) and is collected by filtration, washed with water and dried in air. Afer recrystallization from ethanol/water the title compound is obtained with a melting point of 123°-125° C.

EXAMPLE 16

4-(3'-Pyridylmethoxy)-N,N-dimethylaniline

By following the procedure of Example 15, but replacing 4-(4'-pyridylmethoxy)aniline with 3-(4'-pyridylmethoxy)aniline (prepared as described in Example 4, part B), the title compound is obtained. It is isolated as the dihydrochloride with a melting point of 211°-213° C.

EXAMPLE 17

2,3-Dichloro-4-(4'-pyridylmethoxy)-N,N-dimethylaniline

By following the procedure of Example 15, but replacing 4-(4-pyridylmethoxy)aniline with 2,3-dichloro-4-(4'pyridylmethoxy)aniline (prepared as described in Example 14, part B), the title compound is obtained with a melting point of 95°-96° C.

EXAMPLE 18

3-(2'-Quinolylmethoxy)-N,N-dimethylaniline

By following the procedure of Example 15, but replacing 4-(4'-pyridylmethoxy)aniline with 3-(2'-quinolylmethoxy)aniline (prepared as described in Example 11, part B), the title compound is obtained. It is isolated as a dihydrate of the dihydrochloride with a melting point of 155° C.

EXAMPLE 19

3(4'-Pyridylmethoxy)-N-methyaniline

To a cooled solution of 3-(4'-pyridylmethoxy)aniline (2.0 g, 10 mmole; prepared as described in Example 4, part B) in hexamethyl phosphoric triamide (10 ml) is added sodium hydrogen carbonate (2.5 g) followed by methyl iodide (1.42 g, 10 mmole), and the mixture is stirred at −5° to −10° C. for about 6 hours. The product is precipitated by dilution with water (about 50 ml) and is collected by filtration, washed with water and dried in air. After recrystallization from ethanol-water, the title compound, identical (IR, analysis, TLC) with the compound prepared as in Example 4, part C, is obtained.

EXAMPLE 20

4-(2'-Quinolymethoxy)-N-methylaniline

By following the procedure of Example 19, but replacing 3-(4'-pyridylmethoxy aniline with 4-(2'-quinolylmethoxy)aniline (prepared as described in Example 10, part B), the title compound, identical (IR, analysis, TLC) with the compound prepared as described in Example 10, part C, is obtained.

EXAMPLE 21

3-(2'-Quinolylmethoxy-N-methylaniline

By following the procedure of Example 19, but replacing 3-(4'-pyridylmethoxy)aniline with 3-(2'-quinolylmethoxy)aniline (prepared as discribed in Example 11, part B), the title compound, identical (IR, analysis, TLC) with the compound prepared as described in Example 11, part C, is obtained.

EXAMPLE 22

4-(2'-Quinolylmethoxy)-N-n-butylaniline

To a solution of 4-(2'-quinolylmethoxy)aniline (2.5 g, 10 mmole; prepared as described in Example 10, part B) in hexamethyl phosphoric triamide (12.5 ml) is added sodium hydrogen carbonate (3.5 g) followed by n-butyl iodide (2.0 g, 11 mmole), and the mixture is stirred at ambient temperature for about 24 hours. The product is precipitated by dilution with water (about 150 ml) and is collected by filtration, washed with water and dried in air. The product is dissolved in ethanol (25 ml) and an excess of 6 N ethanolic hydrochloric acid is added to precipitate the dihydrochloride of the title compound which is obtained as a hydrate having a melting point of 225° C.

EXAMPLE 23

3-(2'-Quinolylmethoxy)-N-n-butylaniline

By following the procedure of Example 22, but replacing 4-(2'-quinolylmethoxy)aniline with 3-(2'-quinolylmethoxy)-aniline (prepared as described in Example 11, part B), the title compound is obtained as the dihydrochloride with a melting point of 218° C.

EXAMPLE 24

4-(4'-Pyridylmethoxy)-N-n-butylaniline

A mixture of 4-(4'-pyridylmethoxy)aniline hydrate (3.3 g; prepared as described in Example 1, part B), n-butanal (1.1 g), sodium acetate (1.5 g) and ethanol (40 ml) is hydrogenated in the presence of PtO$_2$ (50 mg). After about 3–5 hours, the theoretical amount of hydrogen has been absorbed and the uptake becomes negligible. The catalyst is removed by filtration, and the filtrate is evaporated in vacuo. The remaining material is partitioned between water and ethyl acetate, and the organic layer is separated, dried and evaporated in vacuo. The resulting product is purified by chromatography (SiO₂, diethyl ether), and the title compound is, after treatment with ethanolic hydrochloric acid by analogy to the method of Example 22, obtained as the dihydrochloride with a melting point of 234° C.

EXAMPLE 25

4-(3'-Pyridylmethoxy)-N-n-butylaniline

By following the precedure of Example 24, but replacing 4-(4'-pyridylmethoxy)aniline with 4-(3'-pyridylmethoxy)-aniline (prepared as described in Example 2, part B), the title compound is obtained with a melting point of 81°-82° C.

EXAMPLE 26

4-(2'-Pyridylmethoxy)-N-n-butylaniline

By following the procedure of Example 24, but replacing 4-(4'-pyridylmethoxy)aniline with 4-(2'-pyridylmethoxy)aniline (prepared as described in Example 3, part B), the title compound is obtained. It is isolated as the dihydrochloride with a melting point of 209°-210° C.

EXAMPLE 27

3-(4'-Pyridylmethoxy)-N-n-butylaniline

By following the procedure of Example 24, but replacing 4-(4'-pyridylmethoxy)aniline with 3-(4'-pyridylmethoxy)aniline (prepared as described in Example 4, part B), the title compound is obtained. It is isolated as a dihydrate of the dihydrochloride with a melting point of 165° C.

EXAMPLE 28

3-(3'-Pyridylmethoxy)-N-n-butylaniline

By following the procedure of Example 24, but replacing 4-(4'-pyridylmethoxy)aniline with 3-(3'-pyridylmethoxy)aniline (prepared as described in Example 5, part B), the title compound is obtained with a melting point of 46°-48° C.

EXAMPLE 29

2,3-Dichloro-4-(4'-pyridylmethoxy)-N-n-butylaniline

By following the procedure of Example 24, but replacing 4-(4'-pyridylmethoxy)aniline with 2,3-dichloro-4-(4'-pyridylmethoxy)aniline (prepared as described in Example 14, part B), the title compound is obtained with a melting point of 80°-82° C.

EXAMPLE 30

4-(2'-Quinolylmethoxy)-N-n-butylaniline

By following the procedure of Example 24, but replacing 4-(4'-pyridylmethoxy)aniline with 4-(2'-quinolylmethoxy)aniline (prepared as described in Example 10, part B, the title compound is obtained identical (IR, analysis, TLC) with the compound prepared as described in Example 22.

EXAMPLE 31

3-(2'-quinolylmethoxy)-N-n-butylaniline

By following the procedure of Example 24, but replacing 4-(4'-pyridylmethoxy)aniline with 3-(2'-quinolylmethoxy)aniline (prepared as described in Example 11, part B), the title compound is obtained identical (IR, analysis, TLC) with the compound prepared as described in Example 23.

EXAMPLE 32

4-(4'-Pyridylmethoxy)-N-benzylaniline

By following the procedure of Example 24, but replacing n-butanal with benzaldehyde, the title compound is obtained with a melting point of 97°-98° C.

EXAMPLE 33

4-(3'-Pyridylmethoxy)-N-benzylaniline

By following the procedure of Example 24, but replacing 4-(4'-pyridylmethoxy)aniline with 4-(3'-pyridylmethoxy)aniline (prepared as described in Example 2, part B) and n-butanal with benzaldehyde, the title compound is obtained with a melting point of 88°-90° C.

EXAMPLE 34

4-(2'-Pyridylmethoxy)-N-benzylaniline

By following the procedure of Example 24, but replacing 4-(4'-pyridylmethoxy)aniline with 4-(2'-pyridylmethoxy)aniline (prepared as described in Example 3, part B) and n-butanal with benzaldehyde, the title compound is obtained with a melting point of 109°-110° C.

EXAMPLE 35

3-(4'-Pyridylmethoxy)-N-benzylaniline

By following the procedure of Example 24, but replacing 4-(4'-pyridylmethoxy)aniline with 3-(4'-pyridylmethoxy)aniline (prepared as described in Example 4, part B) and n-butanal with benzaldehyde, the title compound is obtained with a melting point of 85°-87° C.

EXAMPLE 36

3-(3'-Pyridylmethoxy)-N-benzylaniline

By following the procedure of Example 24, but replacing 4-(4'-pyridylmethoxy)aniline with 3-(3'-pyridylmethoxy)aniline (prepared as described in Example 5, part B) and n-butanal with benzaldehyde, the title compound is obtained. It is isolated as the dihydrochloride with a melting point of 200° C.

EXAMPLE 37

2,3-Dichloro-4-(4'-pyridylmethoxy)-N-benzylaniline

By following the procedure of Example 24, but replacing 4-(4'-pyridylmethoxy)aniline with 2,3-dichloro-4-(4'-pyridylmethoxy)aniline (prepared as described in Example 14, part B) and n-butanal with benzaldehyde, the title compound is obtained with a melting point of 119°-120° C.

EXAMPLE 38

4-(2'-Quinolylmethoxy)-N-benzylaniline

By following the procedure of Example 24, but replacing 4-(4'-pyridylmethoxy)aniline with 4-(2'-quinolylmethoxy)aniline (prepared as described in Example 10, part B) and n-butanal with benzaldehyde, the title compound is obtained with a melting point of 96°-98° C.

EXAMPLE 39

3-(2'-Quinolylmethoxy)-N-benzylaniline

By following the procedure of Example 24, but replacing 4-(4'-pyridylmethoxy)aniline with 3-(2'-quinolylmethoxy)aniline (prepared as described in Example 11, part B) and n-butanal with benzaldehyde, the title compound is obtained. It is isolated as a hemihydrate of the dihydrochloride with a melting point of 212° C.

EXAMPLE 40

3-(4'-Pyridylmethoxy)-N-benzylaniline

A mixture of 3-(4'-pyridylmethoxy)aniline (2.0 g; prepared as described in Example 4, part B), benzaldehyde (1.6 g) and methanol (25 ml) is stirred at ambient temperature for 20 hours and is then refluxed for a further 1 hour. After cooling, sodium borohydride (2.0 g) is added in portions during about 1 hour, keeping the temperature of the reaction mixture between 15° and 20° C. by external cooling. The mixture is stirred at ambient temperature for further 5 hours, whereafter the excess of 4N hydrochloric acid is added carefully, and the acidified mixture is stirred at ambient temperature for a further 16-20 hours. The resulting mixture is extracted twice with ethylacetate, and the combined extracts are dried and evaporated in vacuo. The resulting product is recrystallized (ethanol-water) to yield the title compound, identical (IR, analysis, TLC) with the compound prepared as described in Example 35.

EXAMPLE 41

3-(2'-Quinolylmethoxy)-N-benzylaniline

By following the procedure of Example 40, but replacing 3-(4'-pyridylmethoxy)aniline with 3-(2'-quinolylmethoxy)aniline (prepared as described in Example 11, part B), the title compound is obtained. It is isolated as a hemihydrate of the dihydrochloride, identical (IR, analysis, TLC) with the compound prepared as described in Example 39.

EXAMPLE 42

4-(2'-Pyridylmethoxy)-N-benzylaniline

By following the procedure of Example 40, but replacing 3-(4'-pyridylmethoxy)aniline with 4(2'-pyridylmethoxy)aniline (prepared as described in Example 3, part B), the title compound is obtained, identical (IR, analysis, TLC) with the compound as prepared as in Example 34.

EXAMPLE 43

3-(4'-Pyridylmethoxy)-N-(3''-chlorobenzyl)aniline

By following the procedure of Example 40, but replacing benzaldehyde with 3-chlorobenzaldehyde, the title compound is obtained.

EXAMPLE 44

4-(4'-Pyridylmethoxy)-N-(4'''-methoxybenzyl)aniline

By following the procedure of Example 40, but replacing 3-(4'-pyridylmethoxy)aniline with 4-(4'-pyridylmethoxy)aniline (prepared as described in Example 1, part B), and benzaldehyde with 4-methoxybenzaldehyde, the title compound is obtained.

EXAMPLE 45

2,5-Dichloro-4-(2'-pyridylmethylthio)-N-methylaniline

A. 2,5-Dichloro-4-(2'-pyridylmethylthio)aniline

To a stirred and cooled solution of 2,5-dichloro-4-mercaptoaniline (2.5 g) in 2N sodium hydroxide (100 ml) is at 15°-20° C. added 2-chloromethylpyridine hydrochloride (2.1 g) in portions during about 30 minutes. The mixture is then stirred at ambient temperature for a further 1 hour, whereafter the precipitated product is collected by filtration, washed with water and dried in air. After recrystallization from ethanol-water, the title compound is obtained with a melting point of 105°-106° C.

B.

2,5-Dichloro-4-(2'-pyridylmethylthio)-N-methylaniline

By following the procedure of Example 1, part C, but replacing 4-(4'-pyridylmethoxy)aniline with 2,5-dichloro-4-(2'-pyridylmethylthio)aniline, the title compound is obtained with a melting point of 94°-96° C.

EXAMPLE 46

2,5-Dichloro-4-(3'-pyridylmethylthio)-N-methylaniline

A. 2,5-Dichloro-4-(3'-pyridylmethylthio)aniline

By following the procedure of Example 45, part A, but replacing 2-chloromethylpyridine hydrochloride with 3-chloromethylpyridine hydrochloride, the title compound is obtained with a melting point of 136°-138° C.

B. 2,5-Dichloro-4-(3'-pyridylmethylthio)aniline

By following the procedure of Example 19, but replacing 3-(4'-pyridylmethoxy)aniline with 2,5-dichloro-4-(3'-pyridylmethylthio)aniline, the title compound is obtained.

EXAMPLE 47

2,5-Dichloro-4-(4'-pyridylmethylthio)-N-ethylaniline

A. 2,5-Dichloro-4-(4'-pyridylmethylthio)aniline

By following the procedure of Example 1, part A, but replacing 4-acetaminophenol with 2,5-dichloro-4-mercaptoaniline, the title compound is obtained with a melting point of 133°-135° C.

B.

2,5-Dichloro-4-(4'-pyridylmethylthio)-N-ethylaniline

By following the procedure of Example 22, but replacing 4-(2'-quinolylmethoxy)aniline with 2,5-dichloro-4-(4'-pyridylmethylthio)aniline, and n-butyl iodide with ethyl iodide, the title compound is obtained.

EXAMPLE 48

2,6-Dichloro-4-(4'-pyridylmethylthio)-N-isopropylaniline

A. 2,6-Dichloro-4-(4'-pyridylmethylthio)aniline

By following the procedure of Example 1, part C, but replacing 4-acetaminophenol with 2,6-dichloro-4-mercaptoaniline, the title compound is obtained with a melting point of 88°-89° C.

B.

2,6-Dichloro-4-(4'-pyridylmethylthio)-N-isopropylaniline

By following the procedure of Example 22, but replacing 4-(2'-quinolylmethoxy)aniline with 2,6-dichloro-4-(4'-pyridylmethylthio)aniline, and n-butyl iodide with isopropylbromide, the title compound is obtained.

EXAMPLE 49

2,6-Dichloro-4-(3'-pyridylmethylthio)-N-benzylaniline

A. 2,6-Dichloro-4-(3'-pyridylmethylthio)aniline

By following the procedure of Example 45, part A, but replacing 2,5-dichloro-4-mercaptoaniline with 2,6-dichloro-4-mercaptoaniline, and 2-chloromethylpyridine hydrochloride with 3-chloromethylpyridine hydrochloride, the title compound is obtained with a melting point of 97° C.

B.
2,6-Dichloro-4-(3'-pyridylmethylthio)-N-benzylaniline

By following the procedure of Example 40, but replacing 3-(4'-pyridylmethoxy)aniline with 2,6-dichloro-4-(3'-pyridylmethylthio)aniline, the title compound is obtained.

EXAMPLE 50

2,6-Dichloro-4-(2'-quinolylmethylthio)-N-(2'''-methyl-benzyl)aniline

A. 2,6-Dichloro-4-(2'-quinolylmethylthio)aniline

By following the procedure of Example 1, part C, but replacing 4-acetaminophenol with 2,6-dichloro-4-mercaptoaniline, and 4-chloromethylpyridine hydrochloride with 2-chloromethylquinoline hydrochloride, the title compound is obtained with a melting point of 115°–117° C.

B.
2,6-Dichloro-4-(2'-quinolylmethylthio)-N-(2'''-methyl-benzyl)aniline

By following the procedure of Example 40, but replacing 3-(4'-pyridylmethoxy)aniline with 2,6-dichloro-4-(2'-quinolylmethylthio)aniline, and benzaldehyde with 2-methylbenzaldehyde, the title compound is obtained.

EXAMPLE 51

3-Chloro-4-(3'-pyridylmethylthio)-N-methylaniline

A. 3-Chloro-4-(3'-pyridylmethylthio)aniline

To a solution of 4,4'-diamino-2,2'-dichlorodiphenyldisulphide (3.2 g) in dimethylformamide (20 ml) is added sodium dithionite (4.0 g), and the mixture is stirred at ambient temperature for 5–10 minutes. Potassium carbonate (8.4 g) is then added, followed by 3-chloromethylpyridine hydrochloride (3.3 g), and the mixture is stirred at ambient temperature for about 20 hours. The reaction mixture is then diluted with water (about 100 ml), and the precipitated material is extracted twice with ethyl acetate. The combined extracts are dried and evaporated in vacuo, and the resulting product purified by chromatography (SiO$_2$, ethyl acetate) to give the title compound with a melting point of 101°–103° C.

B. 3-Chloro-4-(3'-pyridylmethylthio)-N-methylaniline

By following the procedure of Example 1, part C, but replacing 4-(4'-pyridylmethoxy)aniline with 3-chloro-4-(3'-pyridylmethylthio)aniline, the title compound is obtained.

EXAMPLE 52

3-Chloro-4-(3'-pyridylmethylsulfinyl)-N-methylaniline

A. 3-Chloro-4-(3'-pyridylmethylsulfinyl)aniline

To a stirred mixture of 3-chloro-4-(3'-pyridylmethylthio)aniline (3.8 g, 15 mmole; prepared as described in Example 51, part A) in chloroform (60 ml) is at 5°–10° C. added 3-chloroperbenzoic acid (2.7 g) in portions during 15–30 minutes. After stirring for a further 1 hour, the resulting solution is washed twice with sodium hydrogen carbonate solution and twice with water, and is then dried and evaporated in vacuo. The resulting product is recrystallized from ethanol-water to give the title compound.

B.
3-Chloro-4-(3'-pyridylmethylsulfinyl)-N-methylaniline

By following the procedure of Example 1, part C, but replacing 4-(4'-pyridylmethoxy)aniline with 3-chloro-4-(3'-pyridylmethylsulfinyl)aniline, the title compound is obtained.

EXAMPLE 53

3-Chloro-4-(3'-pyridylmethylsulfonyl)-N-benzylaniline

A. 2-Chloro-4-(3'-pyridylmethylsulfonyl)aniline

To a stirred solution of 3-chloro-4-(3'-pyridylmethylthio)aniline (3.8 g, 15 mmole; prepared as described in Example 51, part A) in glacial acetic acid (75 ml) is at ambient temperature dropwise added hydrogen peroxide (4.0 ml; 30% in water) during about 1 hour. The mixture is stirred at ambient temperature for a further 20 hours and is then diluted water (about 300 ml) to precipitate the reaction product. It is collected by filtration, washed with water, and recrystallized from ethanol-water to give the title compound.

B.
3-Chloro-4-(3'-pyridylmethylsulfonyl)-N-benzylaniline

By following the procedure of Example 40, but replacing 3-(4'-pyridylmethoxy)aniline with 3-chloro-4-(3'-pyridylmethylsulfonyl)aniline, the title compound is obtained.

EXAMPLE 54

4-(2'-Quinolylmethoxy)-N-methylaniline

A mixture of 4-hydroxy-N-methylaniline (3.5 g), 2-chloromethylquinoline hydrochloride (4.3 g), potassium carbonate (4.2 g) and dimethylformamide (100 ml) is stirred at 80°–100° C. for 20 hours and is then poured into ice-water (about 400 ml). The precipitated reaction product is dissolved in ethyl acetate, and the solution is stirred for about 2 hours with a mixture of active carbon and SiO$_2$, filtered, dried and evaporated in vacuo. The resulting material is dissolved in ethanol (30 ml), and an excess of 6N ethanolic hydrochloric acid is added to precipitate the dihydrochloride of the title compound. The compound is obtained as a hemihydrate, identical (IR, analysis, TLC) with the compound prepared as described in Example 10, part C.

EXAMPLE 55

4-(4'-Pyridylmethoxy)-N-methylaniline

By following the procedure of Example 54, but replacing 2-chloromethylquinoline hydrochloride with 4-chloromethylpyridine hydrochloride, the title compound is obtained, identical (IR, analysis, TLC) with the compound prepared as described in Example 1, part C.

EXAMPLE 56

4-(3'-Pyridylmethoxy)-N-methylaniline

By following the procedure of Example 54, but replacing 2-chloromethylquinoline hydrochloride with 3-chloromethylpyridine hydrochloride, the title compound is obtained, identical (IR, analysis, TLC) with the compound prepared as described in Example 1, part C.

EXAMPLE 57

4-(2'-Pyridylmethoxy)-N-methylaniline

By following the procedure of Example 54, but replacing 2-chloromethylquinoline hydrochloride with 2-chloromethylpyridine hydrochloride, the title compound is obtained, identical (IR, analysis, TLC) with the compound prepared as described in Example 3, part C.

EXAMPLE 58

2,3-Dichloro-4-(4'-pyridylmethoxy)-N-n-butylaniline

A. 2,3-Dichloro-4-methoxy-N-n-butylaniline

A mixture of 2,3-dichloro-4-methoxyaniline (19.2 g), n-butylbromide (22.0 g), sodium hydrogen carbonate (40 g) and methylcellosolve (350 ml) is stirred at 95°-100° C. for about 48 hours. The cooled mixture is filtered, and the filtrate is evaporated in vacuo. The remaining material is washed with water and is thereafter recrystallized from ethanol to give the title compound with a melting point of 47°-49° C.

B. 2,3-Dichloro-4-hydroxy-N-n-butylaniline

To a stirred solution of 2,3-dichloro-4-methoxy-N-n-butylaniline (8.5 g) in 1,1,2,2-tetrachloroethane (80 ml) is added anhydrous aluminium chloride (8.5 g), and the mixture is refluxed for about 40 hours. The resulting mixture is poured into ice/water (about 500 ml), and the precipitated material is extracted twice with methylene chloride. The combined extracts are dried and evaporated in vacuo to give the title compound as a heavy oil.

C. 2,3-Dichloro-4-(4'-pyridylmethoxy)-N-n-butylaniline

By following the procedure of Example 54, but replacing 4-hydroxy-N-methylaniline with 2,3-dichloro-4-hydroxy-N-n-butylaniline, and 2-chloromethylquinoline hydrochloride with 4-chloromethylpyridine hydrochloride, the title compound is obtained, identical (IR, analysis, TLC) with the compound prepared as described in Example 29.

EXAMPLES 59–65

By following the procedure of Example 22 and using the appropriate substituted alkyl halogenide, compounds of Table II are obtained.

TABLE II

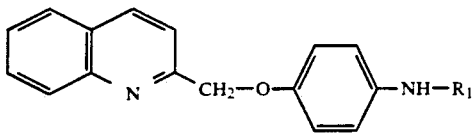

| Ex. No. | R₁ | Melting point | Remarks |
|---|---|---|---|
| 59 | CH$_2$CH$_2$N(C$_2$H$_5$)$_2$ | 217° C. | 3 HCl, H$_2$O |
| 60 | CH$_2$(CH$_2$)$_5$—N(CO)$_2$—C$_6$H$_4$ | 112–114° C. | |
| 61 | CH$_2$CH$_2$N(CH$_3$)$_2$ | 272° C. | 3 HCl, 2 H$_2$O |
| 62 | CH$_2$CH$_2$CH$_2$N(CH$_3$)$_2$ | 210° C. | 3 HCl, H$_2$O |
| 63 | CH$_2$CH$_2$OH | 221° C. | 2 HCl |
| 64 | CH$_2$CH$_2$COOC$_2$H$_5$ | 193–195° C. | 2 HCl, 0.5 H$_2$O |
| 65 | CH$_2$CH$_2$COOH | 159–161° C. | |

EXAMPLE 66

4-(2'-Quinolylmethoxy)-N-1''-(6''-amino-n-hexyl)aniline

To a stirred solution of 4-(2'-quinolylmethoxy)-N-1''-(6''-phthaloyl-n-hexyl)aniline (1.05 g, prepared as described in Example 60) in a mixture of isopropanol (25 ml) and water (4 ml), sodium borohydride (0.44 g) is added, and the resulting solution is stirred at ambient temperature for about 16 hours. Acetic acid (2.3 ml) is then carefully added, and the mixture refluxed for 2 hours. After addition of 4N hydrochloric acid (5 ml) the solution is evaporated, and the resulting precipitate is crystallized from ethanol. After recrystallization from ethanol, the title compound is obtained as a hydrate of the trihydrochloride with a melting point of 224° C.

EXAMPLE 67

2-(2'-Quinolylmethoxy)-N-benzylaniline

By following the procedure of Example 22, but replacing 4-(2'-quinolylmethoxy)aniline with 2-(2'-quinolylmethoxy)aniline and n-butyliodide with benzylbromide, the title compound is obtained with a melting point of 84°-85° C.

EXAMPLE 68

3-(2'-Pyridylmethoxy)-N-benzylaniline

By following the procedure of Example 22, but replacing 4-(2'-quinolylmethoxy)aniline with 3-2'-(pyridylmethoxy)aniline and n-butyliodide with benzylbromide, the title compound is obtained as a dihydrate of the dihydrochloride with a melting point of 161°-163° C.

EXAMPLES 69–76

By following the procedure of Example 22, and using the appropriate starting materials, compounds of Table III are obtained.

TABLE III

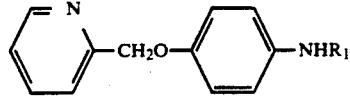

| Ex. No. | R₁ | Melting point | Remarks |
|---|---|---|---|
| 69 | CH$_2$CH$_3$ | 245° C. | 2 HCl |
| 70 | CH$_2$CH$_2$CH$_3$ | 240° C. | 2 HCl |
| 71 | CH(CH$_3$)$_2$ | 240° C. | 2 HCl |
| 72 | (CH$_2$)$_4$CH$_3$ | 200–202° C. | 2 HCl H$_2$O |

TABLE III-continued $$\underset{\text{CH}_2\text{O}}{\overset{N}{\bigcirc}}-\overset{}{\underset{}{\bigcirc}}-\text{NHR}_1$$

| Ex. No. | R₁ | Melting point | Remarks |
|---|---|---|---|
| 73 | (CH₂)₅CH₃ | 198–200° C. | 2 HCl |
| 74 | cyclohexyl | 208° C. | 2 HCl |
| 75 | CH₂CH₂COOC₂H₅ | 130° C. | 2 HCl H₂O |
| 76 | CH₂CH₂COOH | 210° C. | 2 HCl 1.5 H₂O |

EXAMPLE 77

4-(2'-Quinolylmethoxy)-N,N-di-n-propylaniline

By following the procedure of Example 22, but replacing n-butyl iodide with n-propyl iodide, and performing the reaction at 60° C. for about 48 hours using an excess of n-propyl iodide, the title compound is obtained as a hemihydrate of the dihydrochloride with a melting point of 216° C.

EXAMPLE 78

2-Chloro-4-(4'-pyridylmethoxy)-N-benzylaniline

A. 2-Chloro-4-(4'-pyridylmethoxy)acetanilide

By following the procedure of Example 1, part A, but replacing 4-acetaminophenol with 2-chloro-4-hydroxyacetanilide, the title compound is obtained as a hydrate with a melting point of 126°–128° C.

B. 2-Chloro-4-(4'-pyridylmethoxy)aniline

By following the procedure of Example 1, part B, but replacing 4-(4'-pyridylmethoxy)acetanilide with 2-chloro-4-(4'-pyridylmethoxy)acetanilide, the title compound is obtained with a melting point of 120°–121° C.

C. 2-Chloro-4-(4'-pyridylmethoxy)-N-benzylaniline

By following the procedure of Example 40, but replacing 3-(4'-pyridylmethoxy)aniline with 2-chloro-4-(4'-pyridylmethoxy)aniline, the title compound is obtained as a hydrate of the dihydrochloride with a melting point of 234° C.

EXAMPLE 79

3-Chloro-4-(4'-pyridylmethoxy)-N-benzylaniline

A. 3-Chloro-4-(4'-pyridylmethoxy)acetanilide

By following the procedure of Example 1, part A, but replacing 4-acetaminophenol with 3-chloro-4-hydroxyacetanilide, the title compound is obtained as a hydrate with a melting point of 153°–154.5° C.

B. 3-Chloro-4-(4'-pyridylmethoxy)aniline

By following the procedure of Example 1, part B, but replacing 4-(4'-pyridylmethoxy)acetanilide with 3-chloro-4-(4'-pyridylmethoxy)acetanilide, the title compound is obtained with a melting point of 94°–96° C.

C. 3-Chloro-4-(4'-pyridylmethoxy)-N-benzylaniline

By following the procedure of Example 40, but replacing 3-(4'-pyridylmethoxy)aniline with 3-chloro-4-(4'-pyridylmethoxy)aniline, the title compound is obtained as a hemihydrate of the dihydrochloride with a melting point of 238° C.

EXAMPLE 80

2-Methyl-4-(4'-pyridylmethoxy)-N-methylaniline

A. 2-Methyl-4-(4'-pyridylmethoxy)acetanilide

By following the procedure of Example 1, part A, but replacing 4-acetaminophenol with 2-methyl-4-hydroxyacetanilide, the title compound is obtained.

B. 2-Methyl-4-(4'-pyridylmethoxy)aniline

By following the procedure of Example 1, part B, but replacing 4-(4'-pyridylmethoxy)acetanilide with 2-methyl-4-(4'-pyridylmethoxy)acetanilide, the title compound is obtained with a melting point of 140°–141° C.

C. 2-Methyl-4-(4'-pyridylmethoxy)-N-methylaniline

By following the procedure of Example 19, but replacing 3-(4'-pyridylmethoxy)aniline with 2-methyl-4-(4'-pyridylmethoxy)aniline, the title compound is obtained as a hydrate with a melting point of 103° C.

EXAMPLE 81

2-Methyl-4-(2'-quinolylmethoxy)-N-methylaniline

A. 2-Methyl-4-(2'-quinolylmethoxy)acetanilide

By following the procedure of Example 1, part A, but replacing 4-acetaminophenol with 2-methyl-4-hydroxyacetanilide, and 4-chloromethylpyridine hydrochloride with 2-chloromethylquinoline hydrochloride, the title compound is obtained.

B. 2-Methyl-4-(2'-quinolylmethoxy)aniline

By following the procedure of Example 1, part B, but replacing 4-(4'-pyridylmethoxy)acetanilide with 2-methyl-4-(2'-quinolylmethoxy)acetanilide, the title compound is obtained with a melting point of 103°–105° C.

C. 2-Methyl-4-(2'-quinolylmethoxy)-N-methylaniline

By following the procedure of Example 19, but replacing 3-(4'-pyridylmethoxy)aniline with 2-methyl-4-(2'-quinolylmethoxy)aniline, the title compound is obtained as a hydrate of the dihydrochloride with a melting point of 218° C.

EXAMPLE 82

4-Carbethoxy-3-(2'-quinolylmethoxy)-N-methylaniline

A. 4-Carbethoxy-3-(2'-quinolylmethoxy)acetanilide

By following the procedure of Example 1, part A, but replacing 4-acetaminophenol with 4-carbethoxy-3-hydroxyacetanilide, and 4-chloromethylpyridine hydrochloride with 2-chloromethylquinoline hydrochloride, the title compound is obtained as a hydrate with a melting point of 68°–70° C.

B. 4-Carbethoxy-3-(2'-quinolylmethoxy)aniline

By following the procedure of Example 1, part B, but replacing 4-(4'-pyridylmethoxy)acetanilide with 4-carbethoxy-3-(2'-quinolylmethoxy)acetanilide, the title compound is obtained with a melting point of 178°–181° C.

C. 4-Carbethoxy-3-(2'-quinolylmethoxy)-N-methylaniline

By following the procedure of Example 19, but replacing 3-(4'-pyridylmethoxy)aniline with 4-carbethoxy-3-2'-quinolylmethoxy)aniline, the title compound is obtained.

EXAMPLE 83

3-(2'-Quinolylmethoxy)-N-(2''-carboxyphenyl)aniline (2 HCl)

By following the procedure of Example 54, but replacing 4-hydroxy-N-methylaniline with 3-hydroxy-N-(2''-carboxyphenyl)aniline, the title compound is obtained with a melting point of 218°-220° C.

EXAMPLES 84-92

By following the procedures mentioned in Table IV, and using the appropriate starting materials, compounds of Table IV are obtained.

TABLE IV

| Ex. No. | Position of bond | Procedure described in | $R_1$ | Melting point | Remarks |
|---|---|---|---|---|---|
| 84 | 4 | 19 | $CH_3$ | 220° C. | 2 HCl |
| 85 | 4 | 22 | $(CH_2)_3CH_3$ | 239° C. | 2 HCl |
| 86 | 4 | 40 | $CH_2C_6H_5$ | 117-119° C. | |
| 87 | 6 | 54 | $CH_3$ | 145-147° C. | |
| 88 | 6 | 22 | $(CH_2)_3CH_3$ | 200° C. | 2 HCl 0.5 $H_2O$ |
| 89 | 6 | 40 | $CH_2C_6H_5$ | 114-116° C. | |
| 90 | 8 | 54 | $CH_3$ | 101-103° C. | $H_2O$ |
| 91 | 8 | 22 | $(CH_2)_3CH_3$ | 212° C. | 2 HCl |
| 92 | 8 | 40 | $CH_2C_6H_5$ | 200° C. | 2 HCl 1.5 $H_2O$ |

EXAMPLE 93

3-(2'-Quinolylmethoxy)-N-benzyl-N-hydroxymethylaniline ester with N,N-dimethylglycine

A.
3-(2'-Quinolylmethoxy)-N-benzyl-N-hydroxymethylaniline

A mixture of 3-(2'-quinolylmethoxy)-N-benzylaniline (4.2 g, prepared as described in Example 39), 37% aqueous formalin (10 ml), potassium carbonate (6.0 g) and water (50 ml) is stirred at 60° C. for about 20 hours. After cooling, the resulting precipitate is collected by filtration and washed with water to give the title compound.

B.
3-(2'-Quinolylmethoxy)-N-benzyl-N-hydroxymethylaniline ester with N,N-dimethylglycine A suspension of 3-(2'-quinolylmethoxy)-N-benzyl-N-hydroxymethylaniline (3.4 g), dicyclohexylcarbodiimide (2.1 g) and N,N-dimethylglycine (1.1 g) in dry pyridine (25 ml) is stirred at ambient temperature for about 24 hours. The resulting mixture is evaporated in vacuo, and the remaining oil is extracted with dichloromethane (150 ml). After filtration and drying over magnesium sulphate, the dichloromethane is evaporated in vacuo, and the residue triturated with diethyl ether to give the title compound.

EXAMPLE 94

3-(2'-Quinolylmethoxy)-N-benzyl-N-hydroxymethylaniline disodium phosphate ester

A.
3-(2'-Quinolylmethoxy)-N-benzyl-N-chloromethylaniline

A solution of 3-(2'-quinolylmethoxy)-N-benzyl-N-hydroxymethylaniline (8.4 g, prepared as described in Example 93, part A) and phosphorous trichloride (2.5 ml) in dichloromethane (100 ml) is stirred at ambient temperature for 24 hours and is then washed once with water (100 ml) and twice with 5% aqueous sodium carbonate solution (200 ml). The organic layer is separated, dried over magnesium sulphate and evaporated in vacuo to give the crude title compound, which is used in the following step without further purification.

B.
3-(2'-Quinolylmethoxy)-N-benzyl-N-hydroxymethylaniline dibenzyl phosphate ester A mixture of 3-(2'-quinolylmethoxy)-N-benzyl-N-chloromethylaniline (20 mmole, prepared as described in Part A) and silver dibenzylphosphate (15 g) in benzene (350 ml) is refluxed for 2 hours, and is filtered while still hot. The mixture is then extracted with 5% aqueous potassium carbonate solution (300 ml), and the organic layer is separated, dried over magnesium sulphate and evaporated in vacuo. The remaining material is triturated with diethyl ether to give the title compound.

C.
3-(2'-Quinolylmethoxy)-N-benzyl-N-hydroxymethylaniline disodium phosphate ester A solution of 3-(2'-quinolylmethoxy)-N-benzyl-N-hydroxymethylaniline dibenzylphosphate ester (6.0 g) in ethyl acetate (150 ml) is hydrogenated at ambient temperature in the presence of palladium on activated carbon (2.0 g). After 30-60 minutes, the theoretical amount of hydrogen has been absorbed, and the uptake becomes negligible. The catalyst is removed by filtration, and the filtrate is evaporated in vacuo to give crude 3-(2'-quinolylmethoxy)-N-benzyl-N-hydroxymethylaniline phosphate ester. This material is dissolved in methanol (50 ml), and the solution is neutralized with 1N sodium hydroxide solution. The solvent is removed in vacuo, and the residue is triturated with acetone to crystallize the title compound.

EXAMPLE 95

Aerosol

| | |
|---|---|
| 3-(2'-Quinolylmethoxy)-N-benzyl-aniline (active substance) | 1000 mg |
| Sorbitan trioleate | 700 mg |
| Monofluorotrichloromethane | 595 g |
| Difluorodichloromethane | 798 g |

The active substance is micronized in a jet-mill. The majority of the particles should be less than 5 μm in diameter.

A drug concentrate is prepared by dissolving sorbitan trioleate in a small amount of monofluorotrichloromethane and adding the active substance. The concentrate is homogenized carefully. The concentrate is transferred to a sealed tank provided with a refrigeration system. The remaining propellants are added under stirring and cooling to −50° C.

Suitable aerosol containers are filled with the calculated amount of formulation and sealed immediately with metering valves with suitable actuators. Each puff delivers 50 μg of the active substance.

EXAMPLE 96

Capsule

| | |
|---|---|
| 3-(2'-Quinolylmethoxy)-N-benzyl-aniline (active substance) | 100 mg |
| Lactose fine crystalline | 197 mg |
| Magnesium stearate | 3 mg |

The active substance is mixed in a suitable mixer with lactose until a homogeneous state is reached. The magnesium stearate is added and the blending procedure is continued for a few minutes. By means of a suitable capsule-filling machine hard gelatine capsules size 0 are filled, each with 300 mg of the mixture.

EXAMPLE 97

Tablet

| | |
|---|---|
| 3-(2'-Quinolylmethoxy)-N-benzyl-aniline (active substance) | 100 mg |
| Lactose | 75 mg |
| Starch | 12 mg |
| Methylcellulose | 2 mg |
| Sodium carboxymethylcellulose (CMC-Na) | 10 mg |
| Magnesium stearate | 1 mg |

The active substance, lactose and starch are mixed to a homogeneous state in a suitable mixer and moistened with a 5 per cent aqueous solution of methylcellulose 15 cps. The mixing is continued until granules are formed. If necessary, the wet granulation is passed through a suitable screen and dried to a water content of less than 1% in a suitable dryer, e.g. fluid bed or drying oven. The dried granulation is passed through a 1 mm screen and mixed to a homogeneous state with CMC-Na. Magnesium stearate is added and the mixing is continued for a short period of time.

Tablets with a weight of 200 mg are produced from the granulation by means of a suitable tabletting machine.

EXAMPLE 98

Suppository

| | |
|---|---|
| 3-(2'-Quinolylmethoxy)-N-n-butyl-aniline (active substance) | 100 mg |
| Cocoa butter | 1900 mg |

Cocoa butter is slowly heated to form a melt not exceeding 40° C. The active substance is incorporated in the melt, and suppositories with a weight of 2 grams are prepared by moulding.

EXAMPLE 99

Topical Formulation

| | | |
|---|---|---|
| I | 3-(2'-Quinolylmethoxy)-N-benzyl-aniline (active substance) | 2% w/w |
| II | Cetostearyl alcohol | 10% w/w |
| | Liquid paraffin | 10% w/w |
| | White soft paraffin | 5% w/w |
| | Polyoxyethylene sorbitane monostearate | 5% w/w |
| III | Methylparaben | 0.2% w/w |
| | Glycerol | 10% w/w |
| | Water to make | 100% w/w |

The ingredients stated under II are melted together and heated to 70° C. in a vessel fitted with stirrer and homogenizer. In another vessel, the water phase (III) is prepared by heating to 70° C. The water phase is slowly added to the oil phase with continuous stirring and homogenization.

The active substance is added and the temperature is kept for 15 minutes at 70° C. The vessel is cooled to 40° C. under continuous stirring and homogenization. The cooling is continued to a temperature below 25° C. under slow stirring.

EXAMPLE 100

Formulation for Injection

| | |
|---|---|
| 3-(2'-Pyridylmethoxy)-N-benzyl-aniline, 2HCl (active substance) | 1% |
| Sodium chloride | q.s. |
| Water for injection to make | 100% |

The active substance is dissolved in water for injection. The solution is made isotonic with sodium chloride. The solution is filled into ampoules and sterilized.

EXAMPLE 101

Ophthalmic Solution

| | |
|---|---|
| 3-(2'-Quinolylmethoxy)-N-benzyl-aniline, HCl (active substance) | 0.2% |
| Mannitol | 5% |
| Hydroxyethylcellulose | 0.5% |
| Phenyl ethyl alcohol | 0.5% |
| Water for injection to make | 100% |

A 2 per cent concentrate of hydroxyethylcellulose in water for injection including phenyl ethyl alcohol is prepared by slowly spreading the cellulose on the water surface. The concentrate is allowed to stand for complete swelling of the cellulose.

The active substance and mannitol are dissolved in the remaining amount of water for injection.

The solutions are carefully mixed together and sterilized. Under aseptic conditions the solution is filled into suitable sterile containers.

EXAMPLES 102–116

By following the procedure of Example 22, using the appropriate starting materials, and if convenient, replacing hexamethyl phosphoric triamide with dimethyl formamide as solvent, compounds of Table V are obtained.

TABLE V

Structure: quinoline-CH₂O-phenyl-NHR₁ (with positions 2,3,4,5,6 on phenyl)

| Ex. No. | Position of bond | R₁ | Melting point | Remarks |
|---|---|---|---|---|
| 102 | 2 | methyl | 108–110° C. | |
| 103 | 4 | ethyl | 233° C. dec | 2 HCl |
| 104 | 4 | n-propyl | 225° C. dec | 2 HCl |
| 105 | 4 | isopropyl | 85–86° C. | |
| 106 | 2 | n-butyl | 83–84° C. | |
| 107 | 4 | isobutyl | 215° C. dec | 2 HCl |
| 108 | 4 | n-pentyl | 217° C. | 2 HCl |
| 109 | 4 | cyclohexyl | 117–119° C. | |
| 110 | 3 | $CH_2COOH$ | 118–120° C. | Na-salt trihydrate |
| 111 | 3 | $CH_2COOC_2H_5$ | 123–125° C. | |
| 112 | 3 | $CH(CH_3)COOH$ | 91–93° C. | |
| 113 | 3 | $CH(CH_3)COOC_2H_5$ | oil | |
| 114 | 3 | 3-carboxybenzyl | 162–163° C. | |
| 115 | 3 | 2-phenethyl | 205–208° C. | HCl |
| 116 | 3 | (2'-phenyl-2'-hydroxy)ethyl | 153–155° C. | |

EXAMPLES 117–141

By following the procedure of Example 40, using the appropriate starting materials and, if convenient, replacing methanol with ethanol as solvent, compounds of Table VI are obtained.

TABLE VI

| Ex. No. | Position of bond | R₁ | Melting point | Remarks |
|---|---|---|---|---|
| 117 | 3 | 2-methylbenzyl | 186° C. dec. | 2 HCl |
| 118 | 3 | 3-methylbenzyl | 210–212° C. dec | 2 HCl |
| 119 | 3 | 2,6-dichlorobenzyl | 137–138° C. | |
| 120 | 3 | 2-hydroxybenzyl | 164–165° C. | |
| 121 | 3 | 3-hydroxybenzyl | 142–144° C. | |
| 122 | 3 | 4-hydroxybenzyl | 150–152° C. | |
| 123 | 3 | 2,4-dihydroxybenzyl | 175–176° C. dec | |
| 124 | 3 | 2-methoxybenzyl | 110–111° C. | |
| 125 | 3 | 3-methoxybenzyl | 111–113° C. | |
| 126 | 3 | 2-hydroxy-3-methoxybenzyl | 138–140° C. | |
| 127 | 4 | 2-hydroxy-3-methoxybenzyl | 126–127° C. | |
| 128 | 4 | 4-hydroxy-3-methoxybenzyl | 220° C. dec | 2 HCl, 0.5 H₂O |
| 129 | 3 | 3,4,5-trimethoxybenzyl | 208° C. dec | 2 HCl, EtOH |
| 130 | 3 | 2-carboxybenzyl | 132–133° C. | |
| 131 | 4 | 2-carboxybenzyl | 188° C. | |
| 132 | 3 | 4-carboxybenzyl | 198–200° C. | |
| 133 | 4 | 4-carboxybenzyl | 183–185° C. | hydrate |
| 134 | 3 | 4-carbomethoxybenzyl | 198–200° C. | 2 HCl |
| 135 | 3 | 4-carboxamidobenzyl | 106–108° C. | 2 HCl, H₂O |
| 136 | 3 | 2-hydroxy-3-carboxybenzyl | 226° C. dec | 2 HCl |
| 137 | 3 | 2-hydroxy-4-carboxybenzyl | 194–195° C. dec | |
| 138 | 3 | 4-hydroxy-3-carboxybenzyl | 124–126° C. | 2 HCl, 3 H₂O |
| 139 | 3 | 2-hydroxy-5-carboxybenzyl | 188–189° C. | |
| 140 | 3 | 3-cyanobenzyl | 216° C. dec | 2 HCl |
| 141 | 3 | 4-cyanobenzyl | 101–103° C. | HCl |
| 142 | 4 | 4-acetaminobenzyl | 180° C. dec | |
| 143 | 3 | 2-nitrobenzyl | 118–120° C. | HCl, 2 H₂O |
| 144 | 3 | 3-nitrobenzyl | 228–230° C. | 2 HCl, H₂O |
| 145 | 3 | 4-nitrobenzyl | 106–108° C. | HCl, 2 H₂O |
| 146 | 3 | 3-aminobenzyl | 88–90° C. | 3 HCl, 4 H₂O. |
| 147 | 3 | 4-aminobenzyl | 140–142° C. | 3 HCl, 2 H₂O |

The compound described in Example 146 can also be obtained as a napsylate with a melting point of 133°–135° C.

EXAMPLE 148

3-(2'-Quinolylmethoxy)-N-(3''-fluorobenzyl)aniline

A mixture of 3(2'-quinolylmethoxy)acetanilide trihydrate (3.46 g, 10 mmole, prepared as described in Example 11, part A), powdered potassium hydroxide (2.0 g), 3-fluorobenzylbromide (1.6 ml) and acetone (40 ml) is stirred at 50° C. for about 16 hours. After evaporation in vacuo, the residue is treated with water (about 200 ml) and is then extracted with methylene chloride (100 ml). The organic layer is separated and evaporated in vacuo. The residue is dissolved in a mixture of ethanol (20 ml) and 6N hydrochloric acid (20 ml) and is refluxed for about 16 hours. The resulting solution is evaporated in vacuo, and the residue is dissolved in water. The pH of the resulting solution is then adjusted to 10 using aqueous 30% sodium hydroxide. The resulting precipitate is extracted with methylene chloride (50 ml), and the extract is washed with water, dried (MgSO₄) and evaporated in vacuo. The residue is dissolved in a mixture of ethanol and isopropanol, and an excess of isopropanolic hydrochloric acid is added to precipitate the dihydrochloride of the title compound having a melting point of 179°–181° C.

EXAMPLES 149–154

By following the procedure of Example 148, and using the appropriate starting materials, compounds of Table VII are obtained.

TABLE VII

| Ex. No. | Position of bond | R₁ | Melting point | Remarks |
|---|---|---|---|---|
| 149 | 3 | 2-fluorobenzyl | 84–86° C. | |
| 150 | 2 | 3-fluorobenzyl | 84–86° C. | |
| 151 | 4 | 3-fluorobenzyl | 218–219° C. | 2 HCl |

TABLE VII-continued

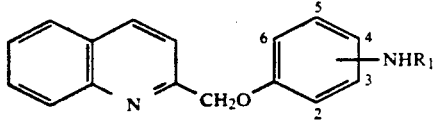

| Ex. No. | Position of bond | $R_1$ | Melting point | Remarks |
|---|---|---|---|---|
| 152 | 3 | 4-fluorobenzyl | 83–84° C. | |
| 153 | 3 | 3-chlorobenzyl | 194–195° C. | 2 HCl |
| 154 | 3 | 3-bromobenzyl | 193–195° C. | 2 HCl |

EXAMPLE 155

3-(2'-Quinolylmethoxy)-N-ethyl-N-methylaniline

To a solution of 3-(2'-quinolylmethoxy)-N-methylaniline (3.4 g, 10 mmole; prepared as described in Example 11, part C) in a mixture of ethanol (80 ml) and 2N sodium hydroxide (30 ml), ethyl iodide (1.0 ml) is added, and the mixture is stirred at ambient temperature for 60 hours. Further ethyl iodide (1 ml each time) is added after approximately 24, 30 and 48 hours, respectively. The resulting solution is evaporated in vacuo, and the residue is partitioned between water (about 100 ml) and ethyl acetate (150 ml). The organic layer is separated, dried (MgSO$_4$) and evaporated in vacuo. The residue is dissolved in ethanol (about 40 ml), and an excess of 6N ethanolic hydrochloric acid is added to precipitate, after dilution with diethyl ether, the dihydrochloride of the title compound having a melting point of 200°–203° C. dec.

EXAMPLE 156-161

By following the procedure of Example 155, and using the appropriate starting materials, compounds of Table VIII are obtained.

TABLE VIII

| Ex. No. | Position of bond | $R_1$ | $R_2$ | Melting point | Remarks |
|---|---|---|---|---|---|
| 156 | 4 | methyl | methyl | 103–105° C. | |
| 157 | 3 | methyl | n-butyl | 185–187° C. dec | 2 HCl |
| 158 | 3 | methyl | benzyl | 92–93° C. | |
| 159 | 3 | CH$_2$COOC$_2$H$_5$ | benzyl | 90–92° C. | |
| 160 | 3 | CH$_2$COOH | benzyl | 174–176° C. | |
| 161 | 4 | n-butyl | n-butyl | 222° C. dec | 2 HCl |

EXAMPLE 162

3-(2'-Quinolylmethoxy)-N,N-di-(3''-fluorobenzyl)aniline

To a solution of 3-(2'-quinolylmethoxy)aniline (2.86 g, 10 mmole; prepared as described in Example 11, part B) in dimethyl formamide (25 ml), potassium carbonate (5.5 g) is added, followed by 3-fluorobenzylbromide (7.6 g, 40 mmole), and the mixture is stirred at 60° C. for about 24 hours. The product is precipitated by dilution with water (about 200 ml) and is then extracted with diethyl ether (about 150 ml). The organic layer is separated, washed with water, charcoaled, dried (MgSO$_4$) and evaporated in vacuo. The resulting oil is dissolved in a mixture of methanol and isopropanol, and an excess of isopropanolic hydrochloric acid is added to precipitate the dihydrochloride of the title compound having a melting point of 164°–166° C.

EXAMPLE 163-165

By following the procedure of Example 162 and using the appropriate starting materials, compounds of Table IX are obtained.

TABLE IX

| Ex. No. | Position of bond | $R_1$ | $R_2$ | Melting point | Remarks |
|---|---|---|---|---|---|
| 163 | 3 | benzyl | benzyl | 170–173° C. | 2 HCl |
| 164 | 3 | benzyl | 3-fluorobenzyl | 167–169° C. | 2 HCl |
| 165 | 4 | 3-fluorobenzyl | 3-fluorobenzyl | 191–193° C. | 2 HCl |

EXAMPLE 166

3-(2'-Quinolylmethoxy)-N-(3''-fluorobenzyl)-N-(4'''-carboxybenzyl)aniline

A.

3-(2'-Quinolylmethoxy)-N-(3''-fluorobenzyl)-N-(4'''-carbethoxybenzyl)aniline

A mixture of 3-(2'-quinolylmethoxy)-N-(3''-fluorobenzyl)aniline (4.31 g, 10 mmole; prepared as described in Example 148), 4-carbethoxybenzyl bromide (3.44 g, 15 mmole), potassium carbonate (5.5 g) and dimethyl formamide (40 ml) is stirred at 60° C. for about 16 hours. After cooling, the mixture is diluted with water (about 200 ml) and is then extracted with diethyl ether (about 100 ml). The organic layer is separated, dried (MgSO$_4$), charcoaled and evaporated in vacuo to give the title compound as an oil.

B.

3-(2'-Quinolylmethoxy)-N-(3''-fluorobenzyl)-N-(4'''-carboxybenzyl)aniline

The material obtained as described in part A is dissolved in a mixture of methanol (50 ml) and 6.2N potassium hydroxide (20 ml), and the solution is refluxed for about 16 hours. After cooling, water (50 ml) is added, and the pH of the resulting solution is adjusted to 5.0 using dilute acetic acid, to precipitate the title compound, which is obtained with a melting point of 159°–161° C.

EXAMPLES 167-170

By following the procedure of Example 166, parts A and B, and using the appropriate starting materials, compounds of Table X are obtained.

TABLE X

![structure: quinoline-CH2O-phenyl-NR1R2 with positions labeled]

| Ex. No. | Position of bond | R₁ | R₂ | Melting point | Remarks |
|---|---|---|---|---|---|
| 167 | 3 | 4-carboxy-benzyl | benzyl | 164–166° C. | |
| 168 | 2 | 4-carboxy-benzyl | 3-fluoro-benzyl | 142–144° C. | |
| 169 | 4 | 4-carboxy-benzyl | 3-fluoro-benzyl | 153–155° C. | |
| 170 | 4 | 4-carbethoxy-benzyl | 3-fluoro-benzyl | oil | |

EXAMPLE 171

3-(2'-Quinolylmethoxy)-N-(2''-carboxyphenyl)aniline

A mixture of 3-(2'-quinolylmethoxy)aniline (200 g; prepared as described in Example 11, part B), 2-brombenzoic acid (240 g), potassium carbonate (200 g), cupriacetate monohydrate (1.2 g) and acetonitrile (4 liter) are refluxed for about 16 hours. After cooling, the mixture is filtered through filter aid, and the resulting filtrate is diluted with water (8 liter), and again filtered through filter aid, whereafter pH of the solution is adjusted to 6.1 using 4N acetic acid. The resulting precipitate is collected by filtration and dried in air. After reprecipitation from methylene chloride-methanol, the title compound is obtained as a hydrate with a melting point of 188°–190° C.

The material can be converted to a hydrate of the dihydrochloride having a melting point of 220°–222° C.

EXAMPLES 172-174

By following the procedure of Example 171 and using the appropriate starting materials, compounds of Table XI are obtained.

TABLE XI

![structure: quinoline-CH2O-phenyl-NHR1]

| Ex. No. | Position of bond | R₁ | Melting point | Remarks |
|---|---|---|---|---|
| 172 | 3 | 2-carbethoxyphenyl | 148–150° C. | HCl |
| 173 | 4 | 2-carboxyphenyl | 218–220° C. | |
| 174 | 3 | 3-carbomethoxyphenyl | 168–170° C. | HCl, 0.5 H₂O |

EXAMPLE 175

3-(2'-Quinolylmethoxy)-N-(2''-carballyloxyphenyl)aniline

A mixture of 3-(2'-quinolylmethoxy)-N-(2''-carboxyphenyl)aniline (7.4 g; prepared as described in Example 171), allyl bromide (2.02 ml), potassium hydrogen carbonate (2.4 g) and dimethyl sulfoxide (30 ml) are stirred at ambient temperature for about 16 hours. The resulting mixture is partitioned between water and diethyl ether, and the organic layer is washed with water, dried (MgSO₄) and charcoaled. An excess of isopropanolic hydrochloric acid is then added to precipitate the hydrochloride of the title compound having a melting point of 136°–138° C.

EXAMPLES 176-180

Salts of the compound described in Example 171 are described in Table XII

TABLE XII

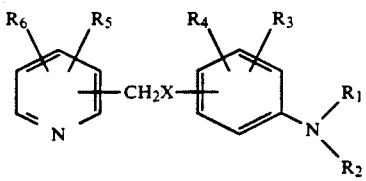

| Ex. No. | M | Melting point | Remarks |
|---|---|---|---|
| 176 | H | 220–222° C. | HCl, 2 H₂O |
| 177 | Na | 146–148° C. | H₂O |
| 178 | K | 98–100° C. | 2 H₂O |
| 179 | ½ Mg | 143–150° C. | 3 H₂O |
| 180 | ½ Ca | 120–130° C. | 3 H₂O |

What we claim is:

1. A compound of the formula I

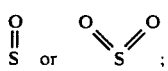

in which formula I X stands for O, S, $$\underset{S}{\overset{O}{\|}} \quad \text{or} \quad \underset{S}{\overset{O \diagdown \diagup O}{\phantom{S}}} \quad ;$$

R₁ and R₂ which can be the same or different stand for hydrogen, straight or branched, saturated or unsaturated, unsubstituted or substituted C₁–C₈-alkyl, aryl or for ar-C₁–C₄-alkyl, aryl and ar being unsubstituted or substituted phenyl, the above substitution being with one or more of the following substituents: halogen, trifluoromethyl, cyano, nitro, amino, carboxy, hydroxy, alkyl, alkoxy; R₃, R₄, R₅, and R₆ are the same or different and stand for hydrogen, halogen, trifluoromethyl, cyano, nitro, amino, carboxy, hydroxy, alkyl, alkoxy; or R₅ and R₆ form an aromatic ring which is fused to the pyridyl ring, and which aromatic ring may be substituted with one of the following: halogen, trifluoromethyl, cyano, nitro, amino, carboxy, hydroxy, lower alkyl, lower alkoxy; provided that R₁ and R₂ cannot be hydrogen at the same time, and provided that when R₅ and R₆ both are chlorine and R₁ is hydrogen, then R₂ cannot be n-propyl; or pharmaceutically acceptable salts esters thereof.

2. A compound according to claim 1, in which R₅ and R₆ in formula I form an aromatic ring fused to the pyridine ring, and the —NR₁R₂ and the

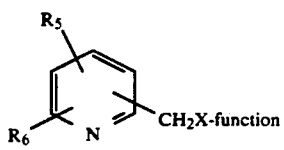

in formula I are placed in meta position to each other.

3. A compound according to claim 2, in which X in formula I is oxygen,

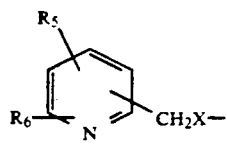

is a 2-quinolylmethoxy radical, and $R_1$ is hydrogen.

4. A compound according to claim 1, which is a salt of a compound of formula I with a pharmaceutically acceptable inorganic or organic acid selected from the group consisting of hydrochloric, hydrobromic and hydroiodic acid, phosphoric acid, sulphuric acid, nitric acid, p-toluenesulphonic acid, methanesulphonic acid, formic acid, acetic acid, propionic acid, citric acid, tartaric acid, and maleic acid.

5. A compound according to claim 1, which is an ester of an N-hydroxymethyl derivative of a compound of formula I.

6. A compound according to claim 1, which is 3-(2'-quinolylmethoxy)-N-benzylaniline and its pharmaceutically acceptable salts.

7. A compound according to claim 1, which is 3-(2'-quinolylmethoxy)-N-methylaniline and its pharmaceutically acceptable salts.

8. A compound according to claim 1, which is 3-(2'-quinolylmethoxy)-N-n-butylaniline and its pharmaceutically acceptable salts.

9. A compound according to claim 1, which is 3-(2'-pyridylmethoxy)-N-benzylaniline and its pharmaceutically acceptable salts.

10. A compound according to claim 1, which is 4-(2'-quinolylmethoxy)-N-1'''-(6''-phthalimido-n-hexyl)aniline and its pharmaceutically acceptable salts.

11. A compound according to claim 1 which is 3-(2'-quinolylmethoxy)-n-(2''-carboxyphenyl)aniline and pharmaceutically acceptable salts thereof.

12. A composition containing an effective amount of at least one member selected from the group consisting of compounds of the formula I and non-toxic, pharmaceutically acceptable salts, as defined in claim 1, together with solid or liquid pharmaceutical carriers and/or auxiliary agents.

13. A method of inhibiting 5-lipoxygenases which comprises administering to a subject in need of such inhibitor, an effective amount of a compound according to claim 1.

* * * * *

UNITED STATES PATENT AND TRADEMARK OFFICE
CERTIFICATE OF CORRECTION

PATENT NO. : 5,109,009  
DATED : April 28, 1992  
INVENTOR(S) : Nielsen, et al

Page 1 of 2

It is certified that error appears in the above-indentified patent and that said Letters Patent is hereby corrected as shown below:

On the title page: Item [63] change

"Continuation of Ser. No. 140,277, Dec. 31, 1987, abandoned, which is a continuation-in-part of Ser. No. 834,542, Feb. 28, 1986." to --[63] Continuation of Ser. No. 140,277. Dec. 31, 1987, abandoned, which is a continuation-in-part of Ser. No. 834,542, Feb. 28, 1986, now U.S. Patent 4,826,987--;

UNITED STATES PATENT AND TRADEMARK OFFICE
CERTIFICATE OF CORRECTION

PATENT NO. : 5,109,009
DATED : April 28, 1992
INVENTOR(S) : Nielsen, et al

It is certified that error appears in the above-indentified patent and that said Letters Patent is hereby corrected as shown below:

Column 1, lines 9-10, delete "abandoned" and insert --U.S. Patent 4,826,987--.
Change "[30] Foreign Application Priority Data, June 21, 1990 [GB] United Kingdom....90401759.7"

Signed and Sealed this

Eighth Day of November, 1994

Attest:

BRUCE LEHMAN

Attesting Officer     Commissioner of Patents and Trademarks